(12) United States Patent
Meng

(10) Patent No.: US 7,781,761 B2
(45) Date of Patent: Aug. 24, 2010

(54) SUBSTITUTED ANTHRACENES AND ELECTRONIC DEVICES CONTAINING THE SUBSTITUTED ANTHRACENES

(75) Inventor: Hong Meng, Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 234 days.

(21) Appl. No.: 12/028,573

(22) Filed: Feb. 8, 2008

(65) Prior Publication Data

US 2008/0210933 A1  Sep. 4, 2008

Related U.S. Application Data

(62) Division of application No. 11/265,696, filed on Nov. 2, 2005, now Pat. No. 7,355,199.

(60) Provisional application No. 60/624,555, filed on Nov. 2, 2004.

(51) Int. Cl.
*H01L 51/30* (2006.01)
(52) U.S. Cl. ............ 257/40; 257/E51.025; 257/E51.05
(58) Field of Classification Search ............ 257/40, 257/E51.001, E51.024, E51.027–E51.029, 257/E51.047, E51.049–E51.05; 438/99; 549/29, 42–43; 552/208–209
See application file for complete search history.

(56) References Cited

U.S. PATENT DOCUMENTS

| 6,107,117 A | 8/2000 | Bao et al. |
| 6,452,207 B1 | 9/2002 | Bao |
| 2004/0067387 A1 | 4/2004 | Kim et al. |
| 2004/0119049 A1 | 6/2004 | Heeney et al. |
| 2005/0035333 A1 | 2/2005 | Gerlach |

FOREIGN PATENT DOCUMENTS

| WO | 03/095445 A2 | 11/2003 |
| WO | 2005/005572 A1 | 1/2005 |
| WO | 2005/019198 A1 | 3/2005 |

OTHER PUBLICATIONS

S.M. Sze, Physics of Semiconductor Devices, 2nd Edition, p. 492, John Wiley & Sons (Book Not Included).
Peter Van Zant, Microchip Fabrication, Fourth Edition, Mcgraw-Hill, New York, 2000 (Book Not Included).
M. P. Doyle et al., Alkyl Nitrite Metal Halide Deamination Reactions. 3. Arylation of Olefinic Compounds in the Deamination of Arylamines by Alkyl Nitrites and Copper (II) Halides. A Convenient and Effective Variation of the Meerwein Arylation Reaction, J. Org. Chem., 1977, vol. 42:2431-2436.
Yanagimoto et al., 11, 11, 12,12-Tetracyano-2,6 Anthraquinodimethane (TANT) As a Novel Extensive Electron Acceptor, J. Chem. Soc. Chem. Commun., 1993, vol. 6:519-520.
B. P. Cho et al., Polycyclic Fluoranthene Hydrocarbons. 2. A New General Synthesis, J. Org. Chem., 1987, vol. 52:5668-5678.

(Continued)

*Primary Examiner*—Matthew W Such
(74) *Attorney, Agent, or Firm*—Gail D. Tanzer

(57) ABSTRACT

Substituted anthracene compounds and electronic devices containing the substituted anthracene compounds are provided.

9 Claims, 4 Drawing Sheets

OTHER PUBLICATIONS

T. Ishiyama et al., Palladium (0) Catalyzed Cross Coupling Reaction of Alkoxydiboron With Haloarenes: A Direct Procedure for Arylboronic Esters, J. Org. Chem., 1995, vol. 60:7508-7510.

M. Murata et al., Novel Palladium (0) Catalyzed Coupling Reaction of Dialkoxyborane With Aryl Halides: Convenient Synthetic Route to Arylboronates, J. Org. Chem., 1997, vol. 62:6458-6459.

M. Murata et al., Palladium Catalyzed Borylation of Aryl Halides or Triflates With Dialkoxyborane: A Novel and Facile Synthetic Route to Arylboronates, J. Org. Chem., 2000, vol. 65:164-168.

L. Zhu et al., An Improved Preparation of Arylboronates: Application in One Pot Suzuki Biaryl Synthesis, J. Org. Chem., 2003, vol. 68:3729-3732.

J. K. Still, The Palladium-Catalyzed Cross-Coupling Reactions of Organotin Reagents With Organic Electrophiles, Angew. Chem. Int. Ed. Engl., 1986, vol. 25:508-524.

M. Kumada, Nickel and Palladium Complex Catalyzed Cross-Coupling Reactions of Organometallic Reagents With Organic Halides, Pure Appl. Chem., 1980, vol. 52:669-679.

E. Negishi, Palladium or Nickel Catalyzed Cross Coupling. A New Selective Method for Carbon Bond Formation, Acc. Chem. Res., 1982, vol. 15:340-348.

CRC Handbook of Chemistry and Physics, 81st Edition, 2000 (Book Not Included).

G. Gustafsson et al., Flexible Light-Emitting Diodes Made From Soluble Conducting Polymers, Nature, 1992, vol. 357:477-479.

Y. Wang, Photoconductive Materials, Kiirk-Othmer Encyclopedia of Chemical Technology, Fourth Edition, 1996, vol. 18:837-860.

Ficker et al., Stability of Polythiophene-Based Transistors and Circuits, J. Appl. Phys., 2003, vol. 94:2638-2641.

H. Meng et al., High Performance Stable Organic Thin-Film Field Effect Transistors Based on Nis-5-Alkythiophen-2-Yl-2,6-Anthracene Semiconductors, J. Amer. Chem. Soc., 2005, vol. 127:2406-2407.

S. Ando et al., Novel 9- and N- Type Organic Semiconductors With an Anthracene Unit, Chem. Mater., 2005, vol. 17:1261-1264.

M. Sun, Excited State Properties of Novel P- and N- Type Organic Semiconductors With an Anthracene Unit, Chem. Phys., 2005, vol. 320:155-163.

International Search Report Dated Apr. 18, 2006, International Application No. PCT/US2005/039947, International Filing Date: Nov. 2, 2005.

SUBSTITUTED ANTHRACENES AND ELECTRONIC DEVICES CONTAINING THE SUBSTITUTED ANTHRACENES

RELATED APPLICATION INFORMATION

This is a divisional application of U.S. application Ser. No. 11/265,696, filed on Nov. 2, 2005.

FIELD OF THE INVENTION

This invention relates to substituted anthracene compounds and electronic devices containing the substituted anthracene compounds.

BACKGROUND

There are numerous types of semiconductor devices, including rectifiers, transistors, current limiters, thermistors, p-n junctions, field-effect diodes, Schottky diodes, and so forth. In each semiconductor device, a semiconductor material is combined with one or more metals or insulators to form the device. Semiconductor devices can be prepared or manufactured by known methods such as, for example, those described by Peter Van Zant in Microchip Fabrication, Fourth Edition, McGraw-Hill, New York (2000).

A particularly useful type of transistor, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2nd edition, John Wiley and Sons, page 492). These components can be assembled in a variety of configurations. An organic thin-film transistor (OTFT) is characterized by having an organic semiconductor layer.

U.S. Pat. No. 6,452,207 discloses a class of fluorene oligomer compounds and describes a thin film transistor device, which comprises a semiconductor layer of fluorene oligomer.

Other known organic semiconductors include regioregular poly(3-alkylthiophenes), oligothiophene derivatives, and fused aromatic compounds such as pentacene and tetracene.

US 2004/0067387 discloses substituted anthracenes that exhibit electroluminescent properties. This published patent application also describes organic electroluminescent devices and a method for manufacturing such devices.

The composition, fabrication, and operation of field effect transistors are described in Bao et al., U.S. Pat. No. 6,107,117, the disclosure of which is incorporated herein by reference.

To enable the production of low-cost integrated circuits (IC) for applications such as electronic devices, smart cards, electronic tags, and displays, there exists a need for semiconductor devices that are fabricated from stable organic compounds that also possess desirable semiconductor properties, e.g., high mobility and a high current on/off ratio. Furthermore, there is a need for highly stable compounds that can be incorporated into TFTs at low substrate temperatures and do not need to be handled in an inert atmosphere during the fabrication of TFTs. The present invention is directed to these, and other, important ends.

SUMMARY OF THE INVENTION

One aspect of the present invention is a compound of Formula

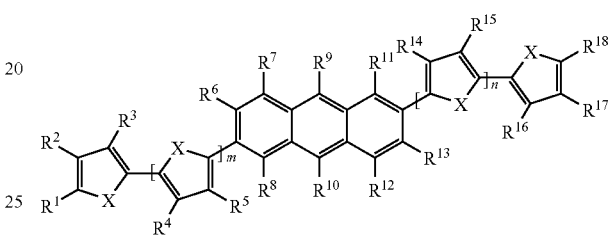

FORMULA 1 wherein m and n are integers selected independently from 0 through 10;

each X is selected independently from O, S, Te, Se and NR;

R1 through R18 are independently selected from hydrogen; substituted or unsubstituted alkyl; substituted or unsubstituted aryl; substituted or unsubstituted heteroaryl; halogen; hydroxy; substituted or unsubstituted aryloxy; substituted or unsubstituted alkoxy; substituted or unsubstituted alkenyl; substituted or unsubstituted alkynyl; substituted or unsubstituted amino; substituted or unsubstituted alkylthio; substituted or unsubstituted phosphino; substituted or unsubstituted silyl; —COR; —COOR; —PO3R2; —OPO3R2; —CN; -CnF2n+1; and CnF2n+1CmH2m+1; and any two adjacent groups, R1-R18 can be taken together to form a ring; and R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted or unsubstituted amino, with the proviso that if X=S, then at least one of R2-R8 or R11-R17 is not H.

In some embodiments, the compound is selected from compounds 1-21:

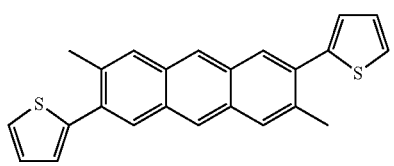

Compound 1

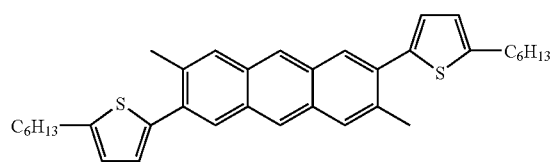

Compound 2

-continued
Compound 3
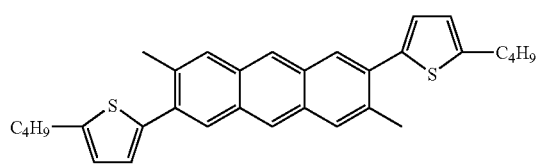
Compound 4
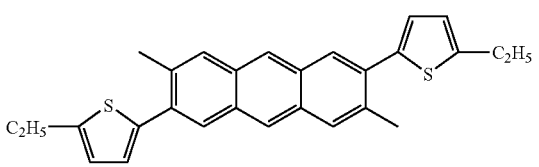
Compound 5
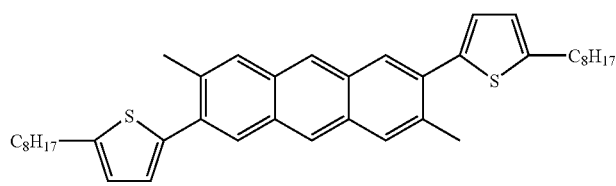
Compound 6
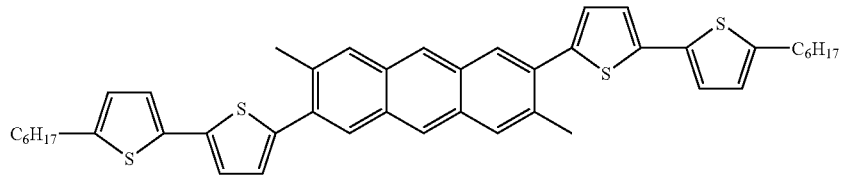
Compound 7
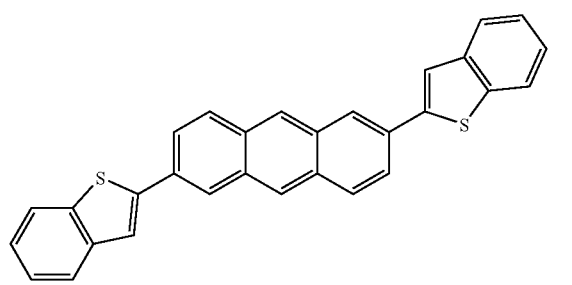
Compound 8
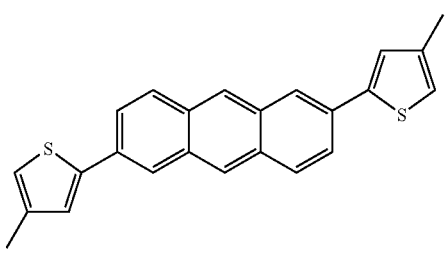
Compound 9 (DTAnt)
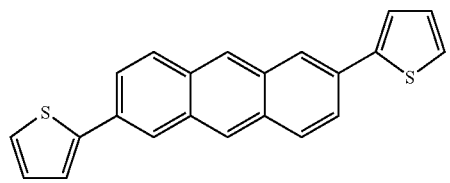
Compound 10 (DHTTAnt)
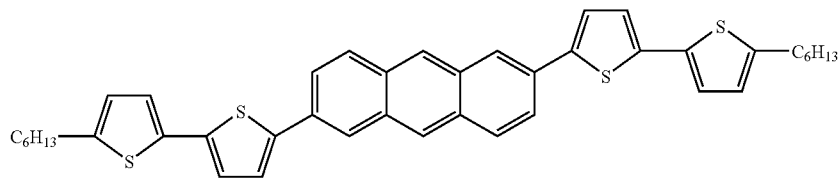
Compound 11 (DEtTAnt)
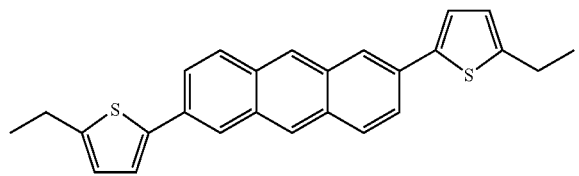
Compound 12 (DOPhTAnt)
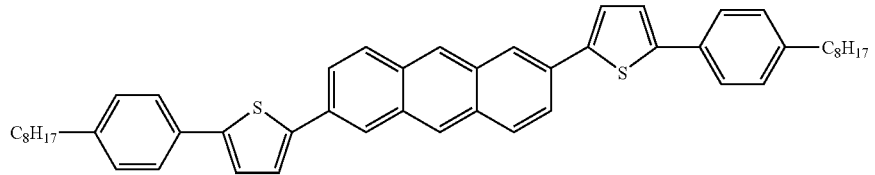

-continued
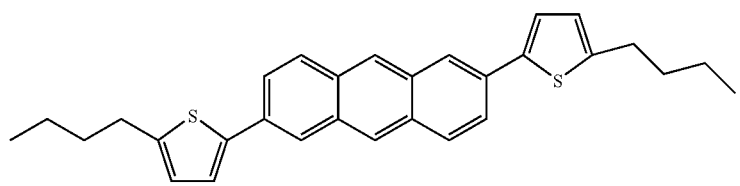
Compound 13 (DBuTAnt)
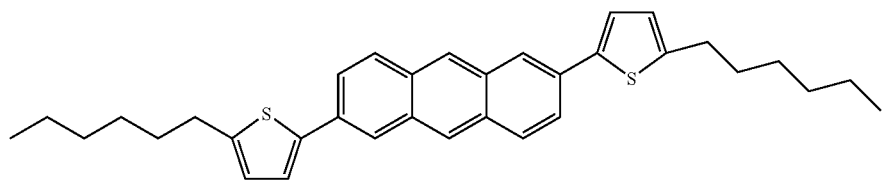
Compound 14 (DHTAnt)
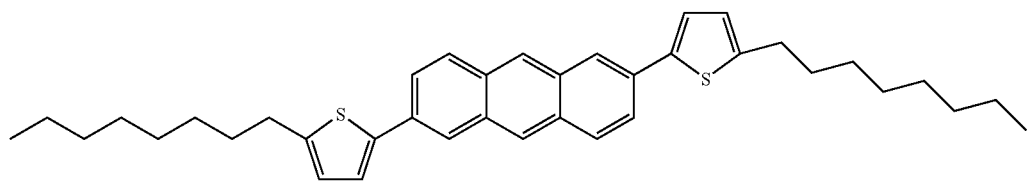
Compound 15 (DOTAnt)
Compound 16 (D3HTAnt)
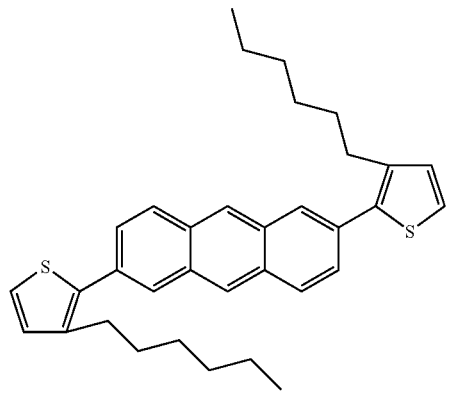
Compound 17 (D4MTAnt)
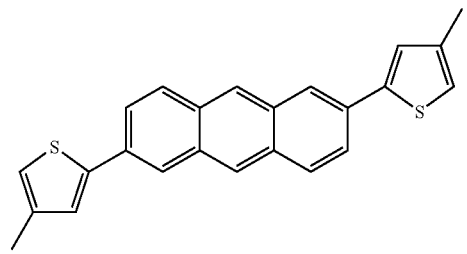
Compound 18 (D4BuTAnt)
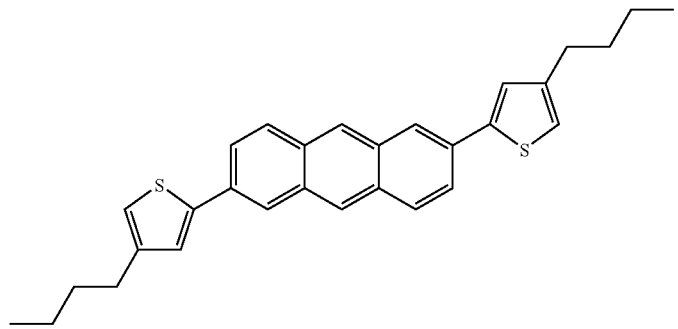

Compound 19 (D4HTAnt)
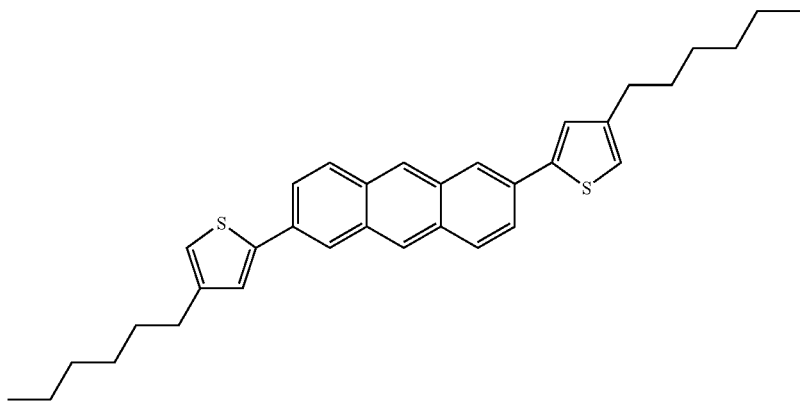
Compound 20 (TAntHT)
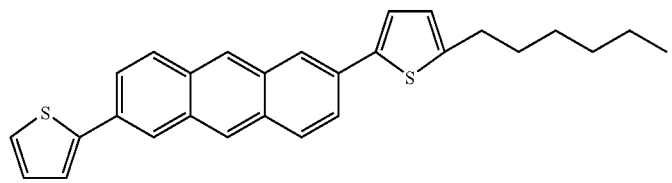
Compound 21 (DTAntESiEt)
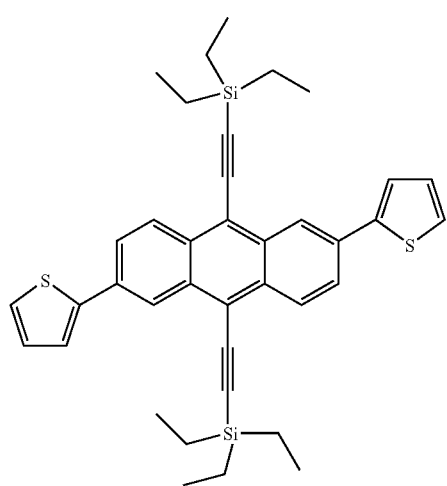

Another aspect of the present invention is an OTFT comprising:
a. a substrate
b. an insulating layer;
c. a gate electrode;
d. a source electrode;
e. a drain electrode; and
f. an organic semiconductor layer comprising a compound of Formula 2,

FORMULA 2

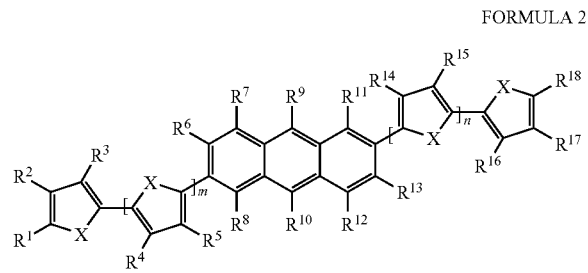

wherein
m and n are integers selected independently from 0-10;
X is selected independently from O, S, Te, Se and NR;
R1-R18 are selected independently from hydrogen; substituted and unsubstituted alkyl; substituted and unsubstituted aryl; substituted and unsubstituted heteroaryl; halogen; hydroxy; substituted and unsubstituted aryloxy; substituted and unsubstituted alkoxy; substituted and unsubstituted alkenyl; substituted and unsubstituted alkynyl; substituted and unsubstituted amino; substituted and unsubstituted alkylthio; substituted and unsubstituted phosphino; substituted and unsubstituted silyl; —COR; —COOR; —PO3R2; —OPO3R2; —CN; -CnF2n+1; and -CnF2n+1CmH2m+1, wherein any two adjacent groups, R1-R18 can be taken together to form a ring; and
R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted or unsubstituted amino and
wherein the insulating layer, the gate electrode, the semiconductor layer, the source electrode and the drain electrode are arranged in any sequence, provided that the gate electrode and the semiconductor layer both contact the insulating layer, the source electrode and the drain electrode both contact the semiconductor layer and the electrodes are separated from each other.

A further aspect of the present invention is an OLED comprising:
a. a substrate;
b. an anode;
c. a layer comprising a compound of Formula 2; and
d. d. a cathode, wherein

FORMULA 2

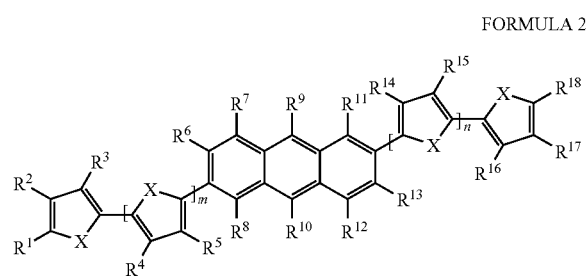

m and n are integers selected independently from 0-10;
X is selected independently from O, S, Te, Se and NR;
R1-R18 are selected independently from hydrogen; substituted or unsubstituted alkyl; substituted or unsubstituted aryl; substituted or unsubstituted heteroaryl; halogen; hydroxy; substituted or unsubstituted aryloxy; substituted or unsubstituted alkoxy; substituted or unsubstituted alkenyl; substituted or unsubstituted alkynyl; substituted or unsubstituted amino; substituted or unsubstituted alkylthio; substituted or unsubstituted phosphino; substituted or unsubstituted silyl; —COR; —COOR; —PO3R2; —OPO3R2; —CN; -CnF2n+1; and -CnF2n+1CmH2 m+1, wherein any two adjacent groups, R1-R18 can be taken together to form a ring; and
R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted and unsubstituted amino.

These and other aspects of the present invention will be apparent to those skilled in the art in view of the following description and the appended claims.

DETAILED DESCRIPTION

Figure 1A:
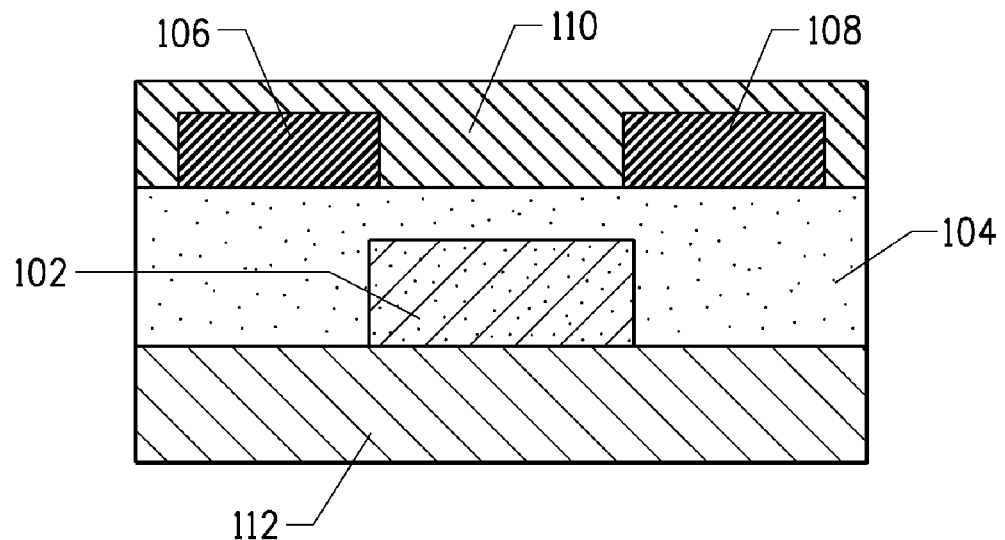
FIG. 1A is a schematic diagram of an organic field effect transistor (OTFT) showing the relative positions of the active layers of such a device in bottom contact mode.

The term 'alkyl' or 'unsubstituted alkyl', whether as part of another term or used independently, denotes straight chain or branched chain, saturated hydrocarbon radicals such as methyl, ethyl, propyl, butyl, hexyl, decanyl, and the like. The term 'substituted alkyl' denotes alkyl that is mono- or poly-substituted with the same or different substituent groups.

The term 'aryl' or 'unsubstituted aryl', whether as part of another term or used independently, refers to a single or multiple aromatic hydrocarbon rings. In the case of multiple rings, two or more rings are fused or linked without an intervening aliphatic chain. Examples of aryl groups include phenyl, biphenyl, terphenyl, naphthyl, anthracenyl, rubrenyl and perylenyl groups. The term 'substituted aryl' refers to an aryl group that is mono- or poly-substituted with one or more of the same or different substituent groups.

The term 'heteroaryl' or 'unsubstituted heteroaryl', whether as part of another term or used independently, refers to single or multiple aromatic hydrocarbon rings, in which at least one skeletal carbon atom is replaced by an O, S, Te, Se or N atom. In the case of multiple rings, two or more rings are fused or linked without an intervening aliphatic chain. For example, heteroaryl groups include oxazolyl, imidazolyl, thiazolyl, thiopenyl, furanyl, pyridyl, pyrimidyl, and pyrrolyl groups. The term 'substituted heteroaryl' refers to a heteroaryl group, which is mono- or poly-substituted with one or more of the same or different substituent groups.

The term 'aryloxy' or 'unsubstituted aryloxy', whether as part of another term or used independently, denotes groups having an oxygen radical substituted with an aryl group. For example, aryloxy groups include phenyloxy, naphthyloxy, anthracenyloxy, and biphenyloxy. The term 'substituted aryloxy' refers to an aryloxy group that is mono- or poly-substituted with one or more of the same or different substituent groups on the carbon atoms of the alkoxy or the aryl group.

The term 'alkoxy' or 'unsubstituted alkoxy', whether as part of another term or used independently, denotes an oxygen radical substituted with an alkyl group. Examples of alkoxy groups include methoxy, ethoxy, propoxy, butoxy, decanoxy, and dodecanoxy. The term 'substituted alkoxy' refers to an alkoxy group that is mono- or poly-substituted with one or more of the same or different substituent groups.

The term 'alkenyl' or 'unsubstituted alkenyl', whether as part of another term or used independently, denotes straight-chain or branched chain hydrocarbon radicals having one or more double bonds between two neighboring carbon atoms of the radical. Examples of alkenyl groups include vinyl, allyl, butenyl, pentenyl, and heptenyl. The term 'substituted alkenyl' denotes an alkenyl group that is mono- or poly-substituted with one or more of the same or different substituent groups.

The term 'alkynyl' or 'unsubstituted alkynyl', whether as part of another term or used independently, denotes straight-chain or branched chain hydrocarbon radicals having one or more triple bonds between two neighboring carbon atoms of the radical. Examples of alkynyl groups include ethynyl, propynyl, butynyl, hexynyl and heptynyl. The term 'substituted alkynyl' denotes an alkynyl group that is mono- or poly-substituted with one or more of the same or different substituent groups.

The phrase "electronic device" refers to micro- and nano-electronic devices such as, for example, micro- and nano-sized transistors and diodes. Illustrative transistors include for instance thin film transistors, particularly organic field effect transistors.

The term "R1-R18 groups" may be used herein as a shorthand notation intended to encompass each R group in structural formulas 1 and 2 labeled R1, R2, R3, R4, R5, R6, R7, through R18. Similar notations are used herein to refer to ranges of "R" groups labeled with consecutive numerical labels, and, unless otherwise stated, are intended to encompass all such labeled "R" groups within the range.

One embodiment of this invention is a compound represented by Formula 1

FORMULA 1

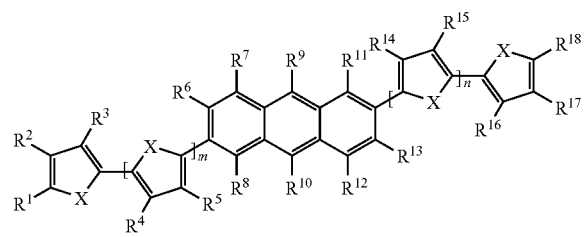

wherein m and n are integers selected independently from 0 through 10;

each X is selected independently from O, S, Te, Se and NR;

R1 through R18 are independently selected from hydrogen; substituted and unsubstituted alkyl; substituted and unsubstituted aryl; substituted and unsubstituted heteroaryl; halogen; hydroxy; substituted and unsubstituted aryloxy; substituted and unsubstituted alkoxy; substituted and unsubstituted alkenyl; substituted and unsubstituted alkynyl; substituted and unsubstituted amino; substituted and unsubstituted alkylthio; substituted and unsubstituted phosphino; substituted and unsubstituted silyl; —COR; —COOR; —PO3R2; —OPO3R2; —CN; -CnF2n+1; and CnF2n+1CmH2m+1; and any two adjacent groups, R1-R18 can be taken together to form a ring; and R is selected from the group of hydrogen; substituted and unsubstituted alkyl; substituted and unsubstituted aryl; substituted and unsubstituted heteroaryl; substituted and unsubstituted alkenyl; substituted and unsubstituted alkynyl; and substituted and unsubstituted amino, with the proviso that if X=S, then at least one of R2-R8 or R11-R17 is not H.

Suitable substituent groups on substituted R and R1-R18 groups in compounds of Formula 1 include cyanide groups; nitro groups; ester groups; ether groups; halogen substitutents; hydroxy groups; alkyl groups; aryl groups; silyl groups; and alkoxy groups.

One embodiment of this invention includes compounds of Formula 1 wherein:
X=S;
n and m are independently selected from 0 or 1;
R3-R16 are independently selected from H; substituted and unsubstituted alkyl; substituted and unsubstituted alkenyl; substituted and unsubstituted alkynyl; and substituted and unsubstituted aryl; and
R1, R2, R17 and R18 are each selected from H; substituted and unsubstituted alkyl; and substituted and unsubstituted aryl; or adjacent groups, R1 and R2, or R17 and R18, are taken together to form a ring.

Specific embodiments of organic semi-conductors of Formula 1 include Compounds 1-21:

Compound 1

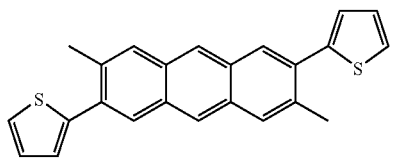

Compound 2

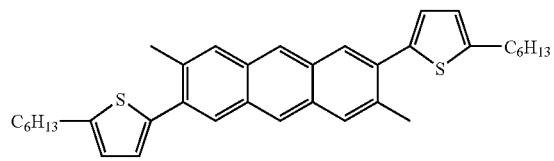

-continued
Compound 3
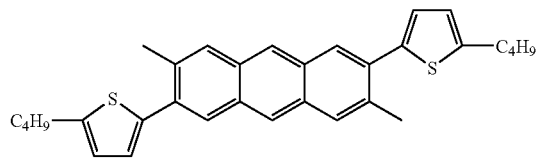
Compound 4
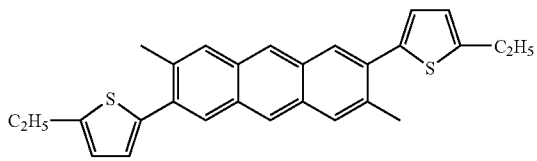
Compound 5
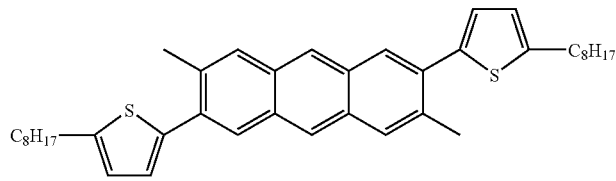
Compound 6
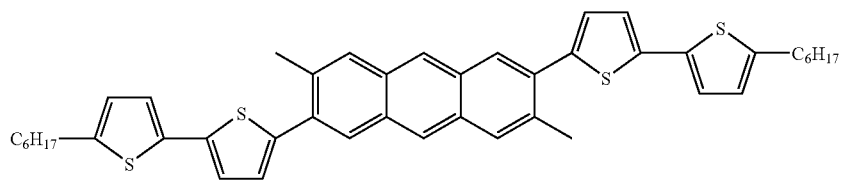
Compound 7
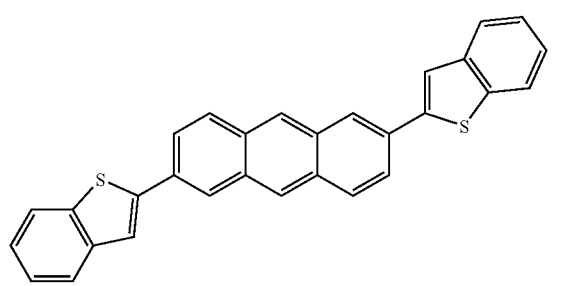
Compound 8
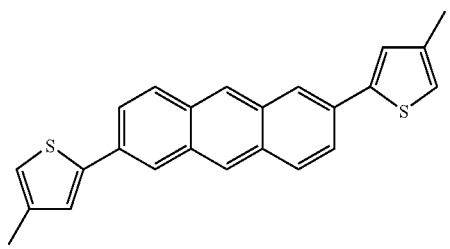
Compound 9 (DTAnt)
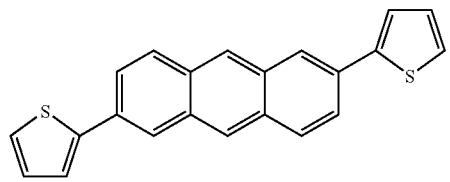
Compound 10 (DHTTAnt)
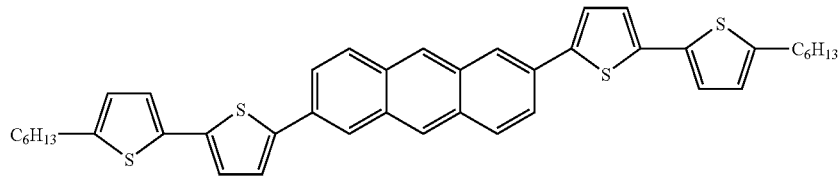
Compound 11 (DEtTAnt)
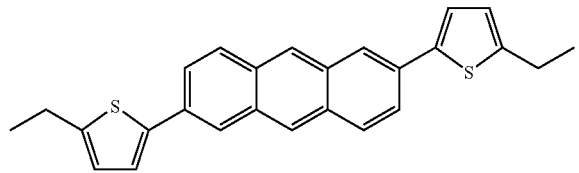
Compound 12 (DOPhTAnt)
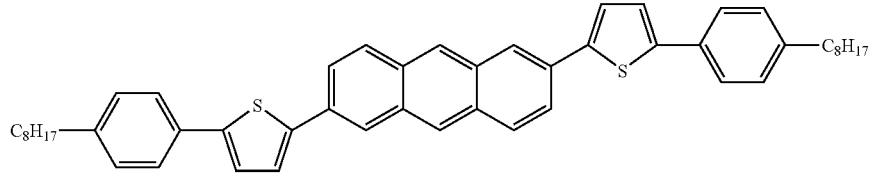

-continued
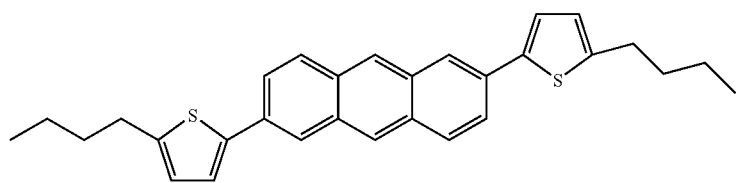
Compound 13 (DBuTAnt)
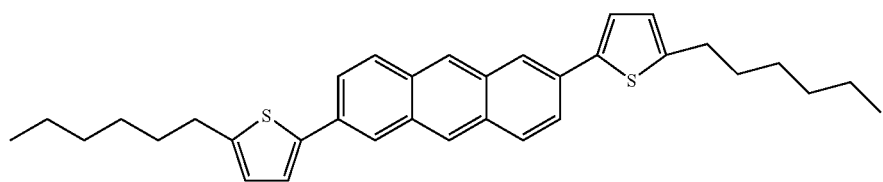
Compound 14 (DHTAnt)
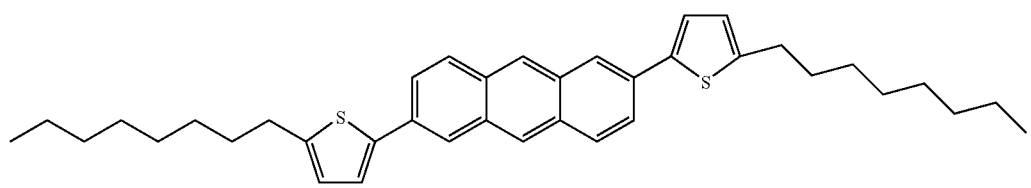
Compound 15 (DOTAnt)
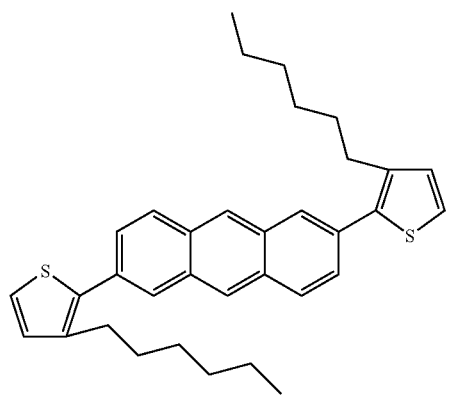
Compound 16 (D3HTAnt)
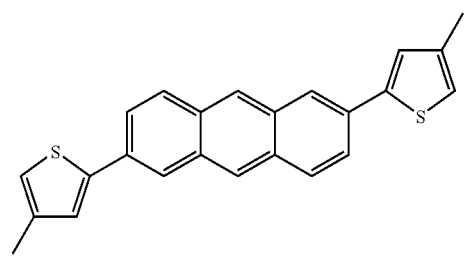
Compound 17 (D4MTAnt)
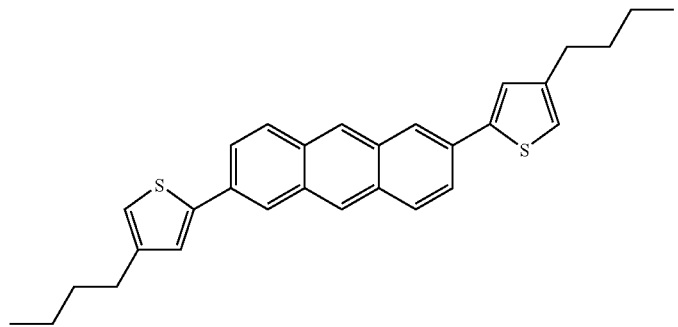
Compound 18 (D4BuTAnt)

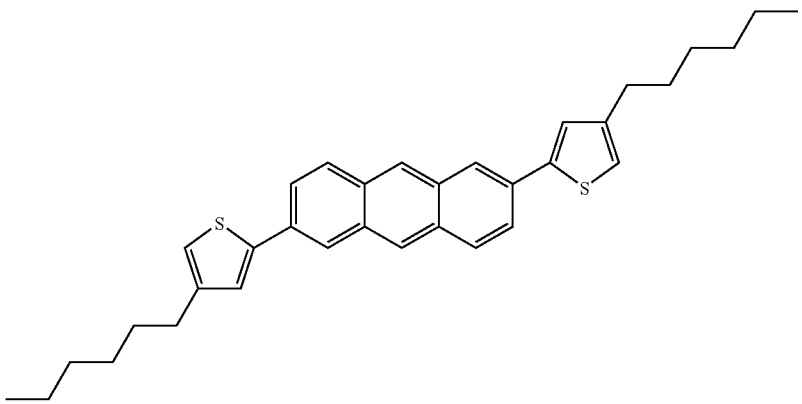

Compound 19 (D4HTAnt)

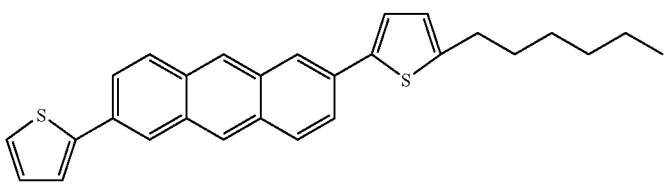

Compound 20 (TAntHT)

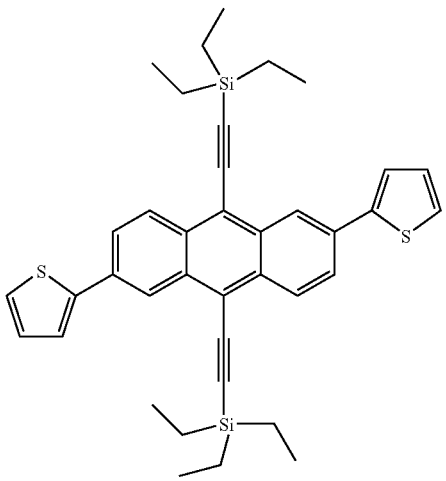

Compound 21 (DTAntESiEt)

Another embodiment of the present invention is a method for synthesizing substituted anthracenes. The method gives organic semiconductor materials that, when incorporated into OTFTs or OLEDs, exhibit desirable characteristics such as high electron mobility (>0.1 cm2/Vs) and high on/off current ratios (>105).

In one embodiment the method comprises reacting a 2,6-dihaloanthracene with a boron reagent in the presence of a palladium catalyst to form a 2,6-disubstituted anthracene; and reacting the 2,6-disubstituted anthracene with a halogenated heterocycle in the presence of a palladium(0) catalyst to form said anthracene.

In a typical synthesis of an organic semiconductor (e.g., a substituted anthracene of Formula 1) made according to this method, a 2,6-dihaloanthraquinone compound (not shown) serves as the starting material and is available commercially or can be prepared, for example, from the corresponding 2,6-diaminoanthraquinone derivative by bromination with CuBr2 (M. P. Doyle et al., J. Org. Chem. 1977, 42, 2462-2431). Other dihaloanthraquinones can be prepared by similar methods to those of M. P. Doyle et al., or by the methods published by T. Yanagimoto et al., J. Chem. Soc. Chem. Commun., (1993), (6), 519-20. Reduction to the corresponding 2,6-dihaloanthracene can be carried out, for example, by reacting the 2,6-dihaloanthraquinone with HI/H3PO2 in acetic acid (B. P. Cho et al. J. Org. Chem. 1987, 52, 5668-5678).

The 2,6-dihaloanthracene (Formula 3) is reacted with a boron reagent in the presence of a suitable catalyst, to form the 2,6-diborate-substituted anthracene (Formula 4), as illustrated below. Suitable reaction conditions, catalysts, bases, and boron reagents are described by T. Ishiyama et al., J. Org. Chem. 1995 60, 7508-7510; M. Murata et al., J. Org. Chem. 1997 62, 6458-6459; M. Murata et al., J. Org. Chem. 2000 65, 164-168; and L. Zhu, et al., J. Org. Chem. 2003 68, 3729-3732.

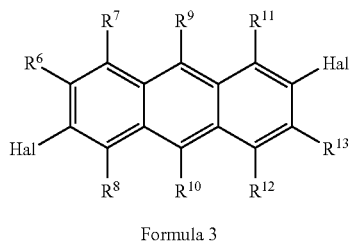

Formula 3

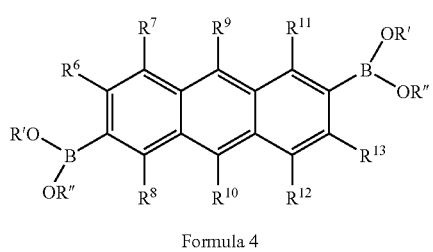

Formula 4

Suitable compounds of Formula 3 include those in which Hal is a halogen;

R6-R13 are selected independently from hydrogen; substituted and unsubstituted alkyl; substituted and unsubstituted aryl; substituted and unsubstituted heteroaryl; hydroxy; substituted and unsubstituted aryloxy; substituted and unsubstituted alkoxy; substituted and unsubstituted alkenyl; substituted and unsubstituted alkynyl; substituted and unsubstituted amino; substituted and unsubstituted alkylthio; substituted and unsubstituted phosphino; substituted and unsubstituted silyl; —COR; —COOR; —PO3R2; —OPO3R2; —CN; -CnF2n+1; and -CnF2n+1CmH2 m+1, wherein any two adjacent groups, R6-R13 can be taken together to form a ring; and R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted and unsubstituted amino.

Suitable boron reagents include boronic acids, boronic esters, dialkoxyboranes and bis(alkoxy)diborons that contain a —B(OR')(OR") group, wherein R' and R" are selected independently from hydrogen; substituted and unsubstituted alkyl; substituted and unsubstituted aryl; substituted and unsubstituted heteroaryl; substituted and unsubstituted alkenyl; substituted and unsubstituted alkynyl; CnF2n+1; and -CnF2n+1CmH2 m+1, and wherein any two adjacent groups, R' and R", can be taken together to form a ring.

Suitable catalysts include Pd(II) complexes such as [1,1'-bis(diphenylphosphino)ferrocene]-dichloropalladium (PdCl2(dppf)); PdCl2(PPh3)2; and palladium acetate. Optionally, the reaction can be carried out in the presence of a mild base such as potassium acetate.

The compound of Formula 4 is reacted with a halogenated heterocycle in the presence of a suitable catalyst (e.g., Pd(PPh3)4 and other similar Pd(0) catalysts, Pd(PAr3)4; PhPdl(PPh3)2; and Pd(OAc)2) to form a compound of Formula 1.

Suitable halogenated heterocycles include compounds of Formula 5

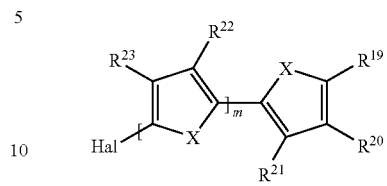

FORMULA 5 wherein
m is an integer selected independently from 0-10;
Hal is a halogen atom;
X is selected independently from O, S, Te, Se and NR;
R19-R23 are selected independently from hydrogen; substituted and unsubstituted alkyl; substituted and unsubstituted aryl; substituted and unsubstituted heteroaryl; hydroxy; substituted and unsubstituted aryloxy; substituted and unsubstituted alkoxy; substituted and unsubstituted alkenyl; substituted and unsubstituted alkynyl; substituted and unsubstituted amino; substituted and unsubstituted alkylthio; substituted and unsubstituted phosphino; substituted and unsubstituted silyl; —COR; —COOR; —PO3R2; —OPO3R2; —CN; -CnF2n+1; and -CnF2n+1CmH2 m+1,
wherein any two adjacent groups, R19-R23 can be taken together to form a ring;
R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted or unsubstituted amino; and
the substituents on substituted R and R19-R23 are functional groups selected independently from cyanide; nitro; ester groups; ether groups; hydroxy; substituted or unsubstituted alkyl; substituted or unsubstituted aryl; and substituted or unsubstituted alkoxy.

Compounds of Formula 5 wherein Hal=Br can be prepared from the corresponding heterocycle by bromination with NBS (N-bromosuccinimide).

A method of preparing compounds of Formula 1 is disclosed hereinbelow in Examples 5 and 6.

Alternatively, the compounds of Formula 1 can be prepared by a method comprising:
a. reacting a heterocycle with a lithium base to form a lithium salt of the heterocycle;
b. reacting the lithium salt of the heterocycle with a boron reagent to form a borate-substituted heterocycle; and
c. reacting the borate-substituted heterocycle with a 2,6-dihalo anthracene in the presence of a palladium(0) catalyst.

In this method, compounds of Formula 1 are prepared by converting a halogenated heterocycle of Formula 5 to the corresponding boron reagent,

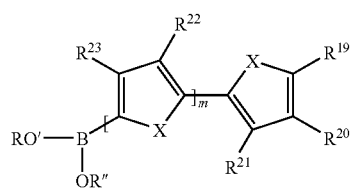

and then reacting that boron reagent with, for example, a 2,6-dibromoanthracene of Formula 3. This method is illustrated in Examples 1-4.

Other C—C coupling reactions, such as the so-called "Stille coupling reactions" (Stille, J. K. Angew. Chem. Int. Ed. Engl. 1986, 25, 508), "Kumada coupling reactions" (Kumada, M. Pure. Appl. Chem. 1980, 52, 669), and "Negishi coupling reactions" (Negishi, E. Acc. Chem. Res. 1982, 15, 340) can also be used to prepare compounds of Formula 1 from the appropriate anthracene and heterocycle derivatives.

Unsymmetrical compounds can be synthesized via a two-stage coupling reaction: For example, in a first coupling reaction, one bromine of 2,6-dibromoanthracene can be replaced by substituted thienyl group A, and a second coupling will replace the other bromine on the anthracene ring with substituted thienyl B.

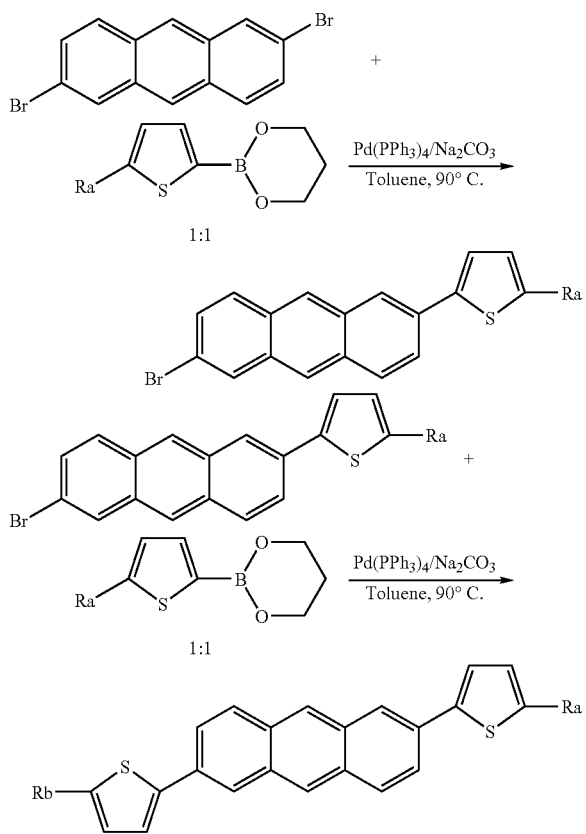

The compounds of Formula 1 have been found to have high mobilities as well as high on/off ratios. The mobilities of these compounds range from 0.01-0.6 cm2/VS. The on/off ratios range from 105-107. These properties of the compounds of Formula 1 make these semiconductor materials suitable for incorporation into semiconductor devices such as thin film transistors (TFT) or field effect transistors (FET) at low substrate temperatures.

The compounds of Formula 1 also show electroluminescent properties and can be used in display devices. The compounds of Formula 1 are highly stable organic semiconductors that can be heated in air up to 300° C. and are also water-stable.

The compounds of Formula 1 that are flat and symmetrical (n=m; Rp=R19-p, p=1-9) are particularly useful in OTFTs. Compounds 1-15 are useful in preparing OTFTs.

Those that are unsymmetrical (i.e., n does not equal m and/or Rp is not the same as R19-p for at least one p, p=1-9), or those having a twisted structure, are particularly useful in OLEDs. Compounds 16-21 shown hereinabove are useful in preparing OLEDs.

Another embodiment of this invention is an OTFT comprising:
a. a substrate
b. an insulating layer;
c. a gate electrode;
d. a source electrode;
e. a drain electrode; and
f. an organic semiconductor layer comprising a compound of Formula 2,

FORMULA 2

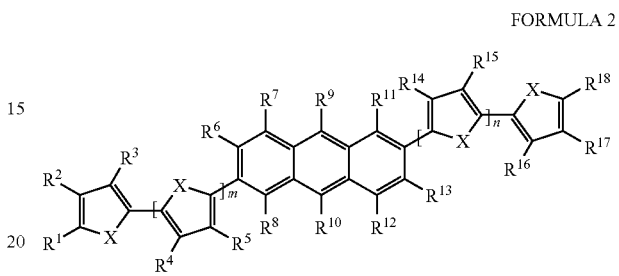

wherein
m and n are integers selected independently from 0-10;
X is selected independently from O, S, Te, Se and NR;
R1-R18 are selected independently from hydrogen; substituted and unsubstituted alkyl; substituted and unsubstituted aryl; substituted and unsubstituted heteroaryl; halogen; hydroxy; substituted and unsubstituted aryloxy; substituted and unsubstituted alkoxy; substituted and unsubstituted alkenyl; substituted and unsubstituted alkynyl; substituted and unsubstituted amino; substituted and unsubstituted alkylthio; substituted and unsubstituted phosphino; substituted and unsubstituted silyl; —COR; —COOR; —PO3R2; —OPO3R2; —CN; -CnF2n+1; and -CnF2n+1CmH2 m+1, wherein any two adjacent groups, R1-R18 can be taken together to form a ring; and R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted or unsubstituted amino; and wherein the insulating layer, the gate electrode, the semiconductor layer, the source electrode and the drain electrode can be arranged in any sequence provided that the gate electrode and the semiconductor layer both contact the insulating layer, the source electrode and the drain electrode both contact the semiconductor layer and the electrodes are not in contact with each other.

Suitable substituent groups on substituted R and R1-R18 groups in compounds of Formula 2 include cyanide groups; nitro groups; ester groups; ether groups; halogen substitutents; hydroxy groups; alkyl groups; aryl groups; and silyl groups.

Compounds of Formula 2 can be prepared by the methods disclosed above for compounds of Formula 1.

In FIG. 1A, there is schematically illustrated an organic field effect transistor (OTFT) showing the relative positions of the active layers of such a device in "bottom contact mode." (In "bottom contact mode" of an OTFT, the drain and source electrodes are deposited onto the gate dielectric layer prior to depositing the active organic semiconductor layer onto the source and drain electrodes and any remaining exposed gate dielectric layer.) A substrate 112 is in contact with a gate electrode 102 and an insulating layer 104 on top of which the source electrode 106 and drain electrode 108 are deposited. Over and between the source and drain electrodes are an organic semiconductor layer 110 comprising a compound of Formula 2.

Figure 1B:
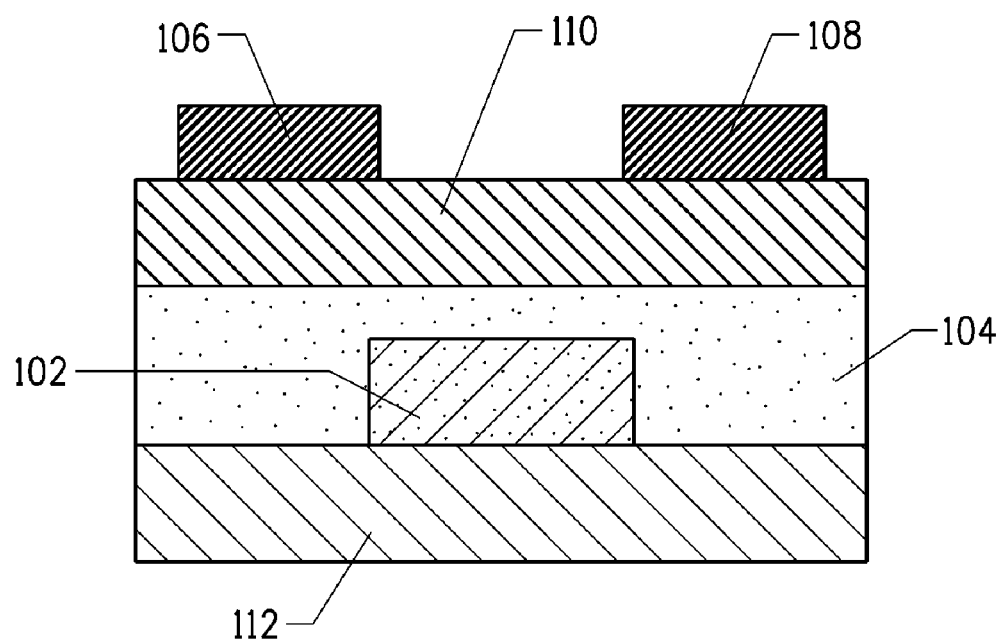
FIG. 1B is a schematic diagram of an OTFT showing the relative positions of the active layers of such a device in top contact mode.

FIG. 1B is a schematic diagram of an OTFT showing the relative positions of the active layers of such a device in top contact mode. (In "top contact mode," the drain and source electrodes of an OTFT are deposited on top of the active organic semiconductor layer.)

Figure 1C:
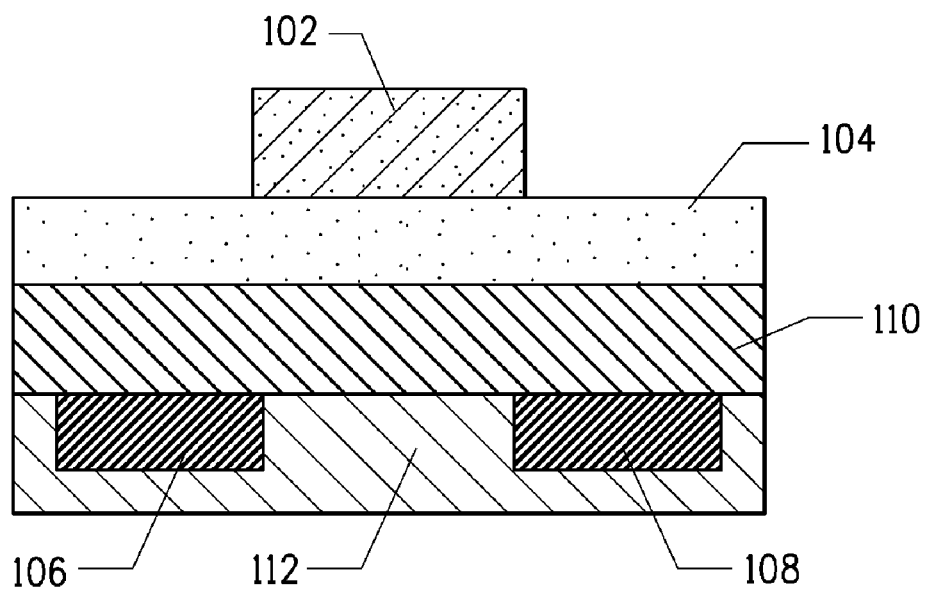
FIG. 1C is a schematic diagram of an organic field effect transistor (OTFT) showing the relative positions of the active layers of such a device in bottom contact mode with the gate at the top.

FIG. 1C is a schematic diagram of OTFT showing the relative positions of the active layers of such a device in bottom contact mode with the gate at the top.

Figure 1D:
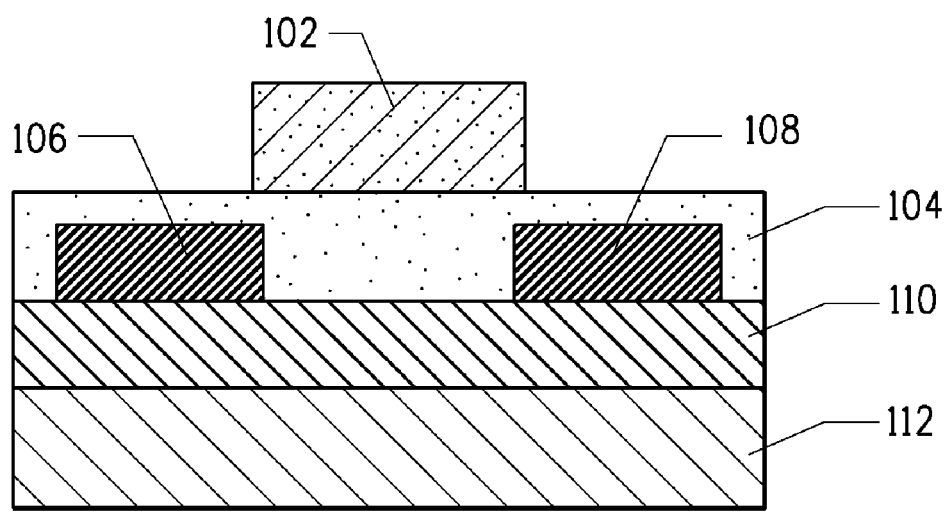
FIG. 1D is a schematic diagram of an organic field effect transistor (OTFT) showing the relative positions of the active layers of such a device in bottom contact mode with the gate at the top.

FIG. 1D is a schematic diagram of an OTFT showing the relative positions of the active layers of such a device in top contact mode with the gate at the top.

The substrate can comprise inorganic glasses, ceramic foils, polymeric materials (for example, acrylics, epoxies, polyamides, polycarbonates, polyimides, polyketones, poly (oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and/or coated metallic foils. The thickness of the substrate can be from about 10 micrometers to over 10 millimeters; for example, from about 50 to about 100 micrometers for a flexible plastic substrate; and from about 1 to about 10 millimeters for a rigid substrate such as glass or silicon. Typically, a substrate supports the OTFT during manufacturing, testing, and/or use. Optionally, the substrate can provide an electrical function such as bus line connection to the source, drain, and electrodes and the circuits for the OTFT.

The gate electrode can be a thin metal film, a conducting polymer film, a conducting film made from conducting ink or paste or the substrate itself, for example heavily doped silicon. Examples of suitable gate electrode materials include aluminum, gold, chromium, indium tin oxide, conducting polymers such as polystyrene sulfonate-doped poly(3,4-ethylenedioxythiophene) (PSS-PEDOT), conducting ink/paste comprised of carbon black/graphite or colloidal silver dispersion in polymer binders. In some OTFTs, the same material can provide the gate electrode function and also provide the support function of the substrate. For example, doped silicon can function as the gate electrode and support the OTFT.

The gate electrode can be prepared by vacuum evaporation, sputtering of metals or conductive metal oxides, coating from conducting polymer solutions or conducting inks by spin coating, casting or printing. The thickness of the gate electrode can be, for example, from about 10 to about 200 nanometers for metal films and from about 1 to about 10 micrometers for polymer conductors.

The source and drain electrodes can be fabricated from materials that provide a low resistance ohmic contact to the semiconductor layer, such that the resistance of the contact between the semiconductor layer and the source and drain electrodes is less than the resistance of the semiconductor layer. Channel resistance is the conductivity of the semiconductor layer. Typically, the resistance should be less than the channel resistance. Typical materials suitable for use as source and drain electrodes include aluminum, barium, calcium, chromium, gold, silver, nickel, palladium, platinum, titanium, and alloys thereof; carbon nanotubes; conducting polymers such as polyaniline and poly(3,4-ethylenedioxythiophene)/poly-(styrene sulfonate) (PEDOT:PSS); dispersions of carbon nanotubes in conducting polymers; dispersions of a metal in a conducting polymer; and multilayers thereof. Some of these materials are appropriate for use with n-type semiconductor materials and others are appropriate for use with p-type semiconductor materials, as is known to those skilled in the art. Typical thicknesses of source and drain electrodes are about, for example, from about 40 nanometers to about 1 micrometer. In some embodiments, the thickness is about 100 to about 400 nanometers.

The insulating layer comprises an inorganic material film or an organic polymer film. Illustrative examples of inorganic materials suitable as the insulating layer include aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of the aforesaid materials can be used for the insulating layer. Illustrative examples of organic polymers for the insulating layer include polyesters, polycarbonates, poly(vinyl phenol), polyimides, polystyrene, poly(methacrylate)s, poly(acrylate)s, epoxy resins and blends and multilayers thereof. The thickness of the insulating layer is, for example from about 10 nanometers to about 500 nanometers, depending on the dielectric constant of the dielectric material used. For example, the thickness of the insulating layer can be from about 100 nanometers to about 500 nanometers. The insulating layer can have a conductivity that is, for example, less than about 10-12 S/cm (where S=Siemens=1/ohm).

The insulating layer, the gate electrode, the semiconductor layer, the source electrode, and the drain electrode are formed in any sequence as long as the gate electrode and the semiconductor layer both contact the insulating layer, and the source electrode and the drain electrode both contact the semiconductor layer. The phrase "in any sequence" includes sequential and simultaneous formation. For example, the source electrode and the drain electrode can be formed simultaneously or sequentially. The gate electrode, the source electrode, and the drain electrode can be provided using known methods such as physical vapor deposition (for example, thermal evaporation or sputtering) or ink jet printing. The patterning of the electrodes can be accomplished by known methods such as shadow masking, additive photolithography, subtractive photolithography, printing, microcontact printing, and pattern coating.

For the bottom contact mode OTFT (FIG. 1A), electrodes 106 and 108, which form channels for source and drain respectively, can be created on the silicon dioxide layer using a photolithographic process. A semiconductor layer 110 is then deposited over the surface of electrodes 106 and 108 and layer 104.

In one embodiment, semiconductor layer 110 comprises one or more compounds represented by Formula 2. The semiconductor layer 110 can be deposited by various techniques known in the art. These techniques include thermal evaporation, chemical vapor deposition, thermal transfer, ink-jet printing and screen-printing. Dispersion thin film coating techniques for deposition include spin coating, doctor blade coating, drop casting and other known techniques.

For top contact mode OTFT (FIG. 1B), layer 110 is deposited on layer 104 before the fabrication of electrodes 106 and 108.

OLEDs

Another embodiment of this invention is an OLED comprising:
  a. a substrate;
  b. an anode;
  c. a layer comprising a compound of Formula 2; and
  d. a cathode.

The OLED can also contain an electron-transport layer, a hole-transport layer, a hole-injection layer and/or an electron-injection layer. The layer comprising a compound of Formula 2 can be used in a luminescent layer or in a hole-transport layer.

Figure 2:
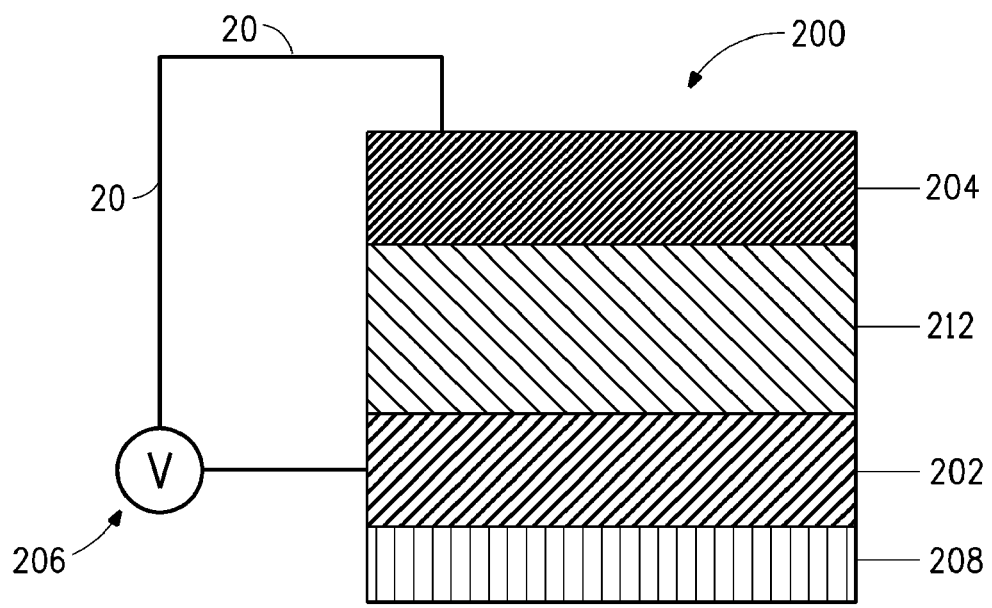
FIGS. 2-4 are schematic representations of OLEDs, in accordance with various embodiments of the invention.

FIG. 2 is a schematic representation of an OLED 200, in accordance with one embodiment of the invention. An anode 202 and a cathode 204 are electrically connected to an electric power supply 206. Electric power supply 206 is preferably a current source. An organic semiconductor layer 212 is between the anode and the cathode. FIG. 2 shows the substrate 208 in contact with the anode. In operation, an electrical current is passed through the OLED 200 by connecting an external current or voltage source with electrical conductors 20 to the anode and the cathode, causing light to be emitted from the semiconductor layer 212.

Figure 3:
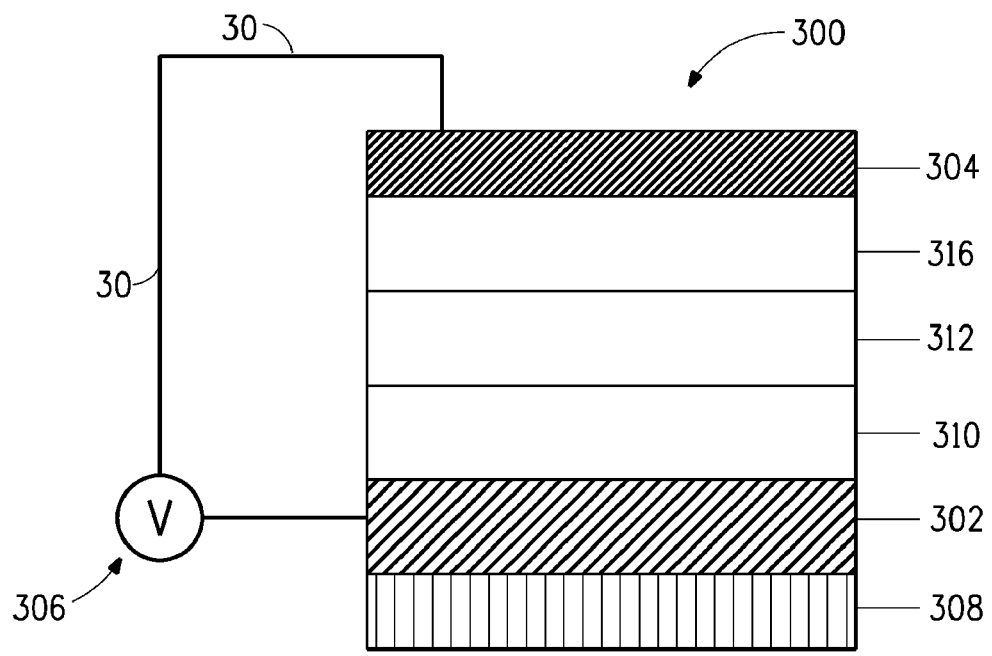

FIG. 3 is a schematic representation of an OLED 300, in accordance with one embodiment of the invention. An anode 302 and a cathode 304 are electrically connected to an electric power supply 306 via electrical conductors 30. Electric power supply 306 is preferably a current source. A hole-transporting layer 310 is present in contact with the anode from one side and an organic semiconductor layer 312 on the other side. Similarly, an electron-transporting layer 316 is present in contact with the cathode on one side and the organic semiconductor layer 312 on the other side. Organic semiconductor layer 312 comprises one or more compounds represented by Formula 1. FIG. 3 shows the substrate 308 in contact with the anode.

Figure 4:
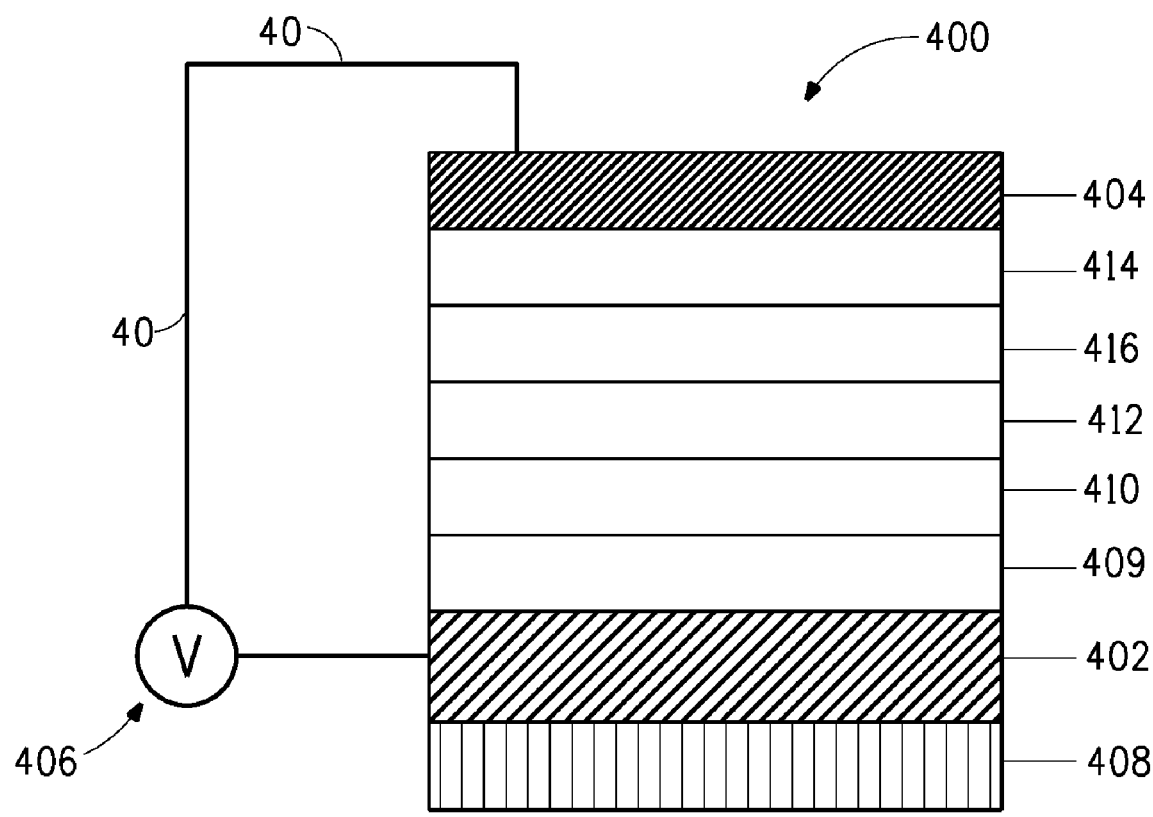

FIG. 4 is a schematic representation of an OLED 400, in accordance with one embodiment of the invention. An anode 402 and a cathode 404 are electrically connected to an electric power supply 406 via electrical conductors 40. Electric power supply 406 is preferably a current source. A hole-injecting layer 409 is present in contact with anode 402. Hole injecting layer 409 facilitates the injection of holes from anode 402 into display device 400. A suitable hole-injecting material is copper phthalocyanine. A hole-transporting layer 410 is present in contact with hole injecting layer 409 from one side and an organic semiconductor layer 412 on the other side. Hole transporting layer 410 facilitates the passage of holes from hole-injecting layer 409 to organic semiconductor layer 412. FIG. 4 shows the substrate 408 in contact with the anode.

Similarly, an electron-injecting layer 414 is present in contact with cathode 404. Electron injecting layer 414 facilitates the injection of electrons from cathode 404 into display device 400. A suitable electron-injecting material is LiF/Al. An electron-transporting layer 416 is present in contact with hole-injecting layer 414 from one side and organic semiconductor layer 412 on the other side. Electron transporting layer 416 facilitates the passage of electrons from electron injecting layer 414 to organic semiconductor layer 412.

Organic semiconductor layer 412 comprises one or more compounds represented by Formula 1.

The anode is an electrode that is particularly efficient for injecting positive charge carriers. It can be made of, for example materials containing a metal, mixed metal, alloy, metal oxide or mixed-metal oxide, or it can be a conducting polymer. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The IUPAC numbering system is used throughout, where the groups from the Periodic Table are numbered from left to right as 1-18 (CRC Handbook of Chemistry and Physics, 81st Edition, 2000). The anode can also comprise an organic material such as polyaniline as disclosed in "Flexible light-emitting diodes made from soluble conducting polymer," Nature vol. 357, pp 477-479 (11 Jun. 1992). At least one of the anode and cathode should be at least partially transparent to allow the generated light to be observed. Other specific examples of suitable anodes include aluminum; gold; chromium; polystyrene sulfonate-doped poly(3,4-ethylenedioxythiophene) (PSS-PEDOT); carbon black or graphite dispersed in a polymer binder; and colloidal silver dispersion in a polymer binder.

Examples of hole-transport materials are disclosed, for example, in Kirk-Othmer Encyclopedia of Chemical Technology, Fourth Edition, Vol. 18, p. 837-860, 1996, by Y. Wang. Either hole-transporting molecules or polymers can be used. Commonly used hole transporting molecules include: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), α-phenyl-4-N,N-diphenylaminostyrene (TPS), p-(diethylamino)-benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9 H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole-transporting polymers include polyvinylcarbazole, (phenylmethyl)polysilane, and polyaniline. It is also possible to obtain hole-transporting polymers by doping hole-transporting molecules such as those recited hereinabove into polymers such as polystyrene and polycarbonate.

Examples of electron-transport materials include metal-chelated oxinoid compounds, such as tris(8-hydroxyquinolato)aluminum (Alq3); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The electron-transport layer can function both to facilitate electron transport, and also serve as a buffer layer or confinement layer to prevent quenching of the exciton at layer interfaces. Preferably, the electron-transport layer promotes electron mobility and reduces exciton quenching.

The cathode is an electrode that injects electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It will be recognized by one skilled in the art that additional layers can be present in organic electronic devices. For example, there can be a layer between the conductive polymer layer and the active layer to facilitate positive charge transport and/or band-gap matching of the layers, or to function as a protective layer. Similarly, there can be additional layers between the active layer and the cathode layer to facilitate negative charge transport and/or band-gap matching between the layers, or to function as a protective layer. In addition, any of the above-described layers can be made of two or more layers. Alternatively, some or all of inorganic anode layer, the conductive polymer layer, the active layer, and cathode layer, may be surface treated to increase charge carrier transport efficiency. It is understood that each functional layer may be made up of more than one layer.

The device can be prepared by sequentially vapor depositing the individual layers on a suitable substrate. Substrates such as glass and polymeric films can be used. Suitable substrates include those described above for OTFTs. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode, 500-5000 Å, preferably 1000-2000 Å; hole transport layer, 50-1000 Å, preferably 200-800 Å; light-emitting layer, 10-1000 Å, preferably 100-800 Å; electron transport layer, 50-1000 Å, preferably 200-800 Å; cathode, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

When electric current is applied to anode and cathode, electrons and holes are injected into the OLED. The electrons and holes combine in organic semiconductor layer and emit light photons due to the electroluminescent properties of the compounds present in organic semiconductor layer.

EXAMPLES

Embodiments of the present invention are described in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General

The structures of the synthesized compounds were confirmed by X-ray crystal structure analysis, NMR, and MS spectrum analysis. Thermo-gravimetric analysis (TGA) was carried out on a TA Instruments Q550 TGA System™ at a heating rate of 10° C./minutes and at a nitrogen flow rate of 60 cm3/min.

Cyclic voltammetry (CV) was performed on an EG&G Parc Model 273ATM potentiostat/galvanostat system with a three-electrode cell in a solution of Bu4NBF4 (0.1 M) in acetonitrile at a scan rate of 50 mV/s.

The semiconductor films were coated on a disc Pt electrode (0.050 cm2) by vacuum sublimation. A Pt wire was used as the counter electrode and an Ag/AgNO3 (0.01 M) electrode was used as the reference electrode. Prior to each series of measurements, the cell was deoxygenated with argon. Organic semiconductor was added in the electrolyte solution (0.2 mg/mL). The electrode's potential was calibrated with the saturated calomel electrode (SCE) by measuring the ferrocene/ferrocenium couple in this system (0.15 V versus SCE). The band gaps were derived from the difference between onset potentials.

X-ray data were taken on a CAD-4 diffractometer with copper K □ radiation, and the structure was solved using the NRCVAX™ suite of programs.

Nuclear magnetic resonance (NMR) spectra were taken on a Bruker™ 500 MHz spectrometer. All chemical shifts were reported relative to tetramethylsilane (TMS) at 0.0 ppm, unless otherwise stated.

Characterization of synthesized compounds included the analyses recited hereinabove.

Unless otherwise stated, all reagents were purchased from Sigma-Aldrich, Inc., St. Louis, Mo.

Device Fabrication

After the oxide layer present on the surface of the wafer is removed from one surface, a Ti—Au layer is evaporated to provide electrical contact. Substrates of wafer 102 are cleaned with isopropanol, acetone, rinsed with de-ionized water, dried in a nitrogen gas stream and then cleaned in oxygen plasma for 5 minutes and UV ozone for 5 minutes. The surface was treated with octyltrichlorosilane (OTS). In one embodiment of the bottom contact devices of the invention, electrodes 106 and 108 have a width (W) of 25-200 □m and length (L) of 2.5-20 □m. In one embodiment of the contact devices of the invention, electrodes 106 and 108 have a width (W) of 400-1000 □m and length (L) of 40-100 □m. In one embodiment of the invention, layer 110 is deposited at a rate of 2-3 Å/s under a pressure of ~2.0×106 torr to a final thickness of 500 Å. A quartz crystal monitor can be used to monitor the growth thickness of layer 110 during deposition. The substrate temperature during deposition is controlled by heating the copper block on which the substrate is mounted. The substrate temperature during deposition (TD) of layer 110 is in the range of 25° C. to 120° C.

Example 1

Synthesis of (2,6-Anthracene-bis-2'-benzothiophene)

This example illustrates the synthesis of an exemplary compound (Compound 7). It will be apparent to one skilled in the art that other compounds represented by Formulas 1 or 2 can be synthesized in a manner similar to that described in Example 1.

COMPOUND 7

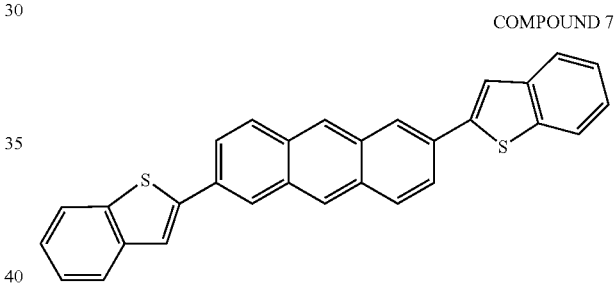

A 500 mL 3-neck round-bottomed flask was charged with anhydrous copper bromide (CuBr2) (56 g, 0.25 mol), t-butyl nitrite (90%, 34 g, 0.30 mol) and anhydrous acetonitrile (300 mL). The mixture was then refluxed at 65° C. for 10 minutes. Thereafter, 2,6-diaminoanthraquinone (Compound 22, 23.8 g, 0.10 mol) was slowly added over period of 30 minutes.

When gas evolution ceased, the reaction mixture was cooled to room temperature and poured into 6 M HCl (500 mL). The precipitate was filtered and washed with water and ethanol. The crude product was then purified by sublimation (~270° C./60 mTorr) to give 33.62 g (92%) of purified product. The product had a mp>280° C. The product was identified as 2,6-dibromoanthraquinone (Compound 23):

COMPOUND 22

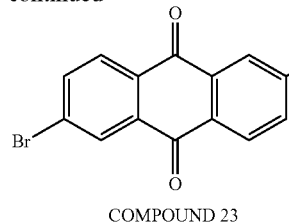

COMPOUND 23

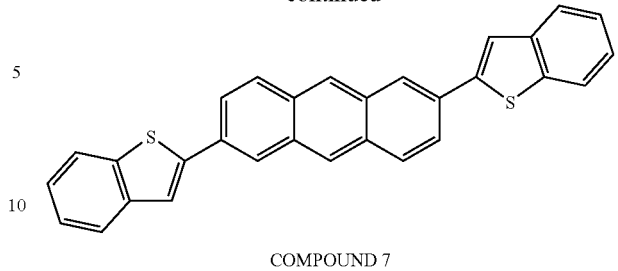

COMPOUND 7

Subsequently, a mixture of 2,6-dibromoanthraquinone (22.41 g, 61.23 mmol), acetic acid (250 mL), 56-58% hydriodic acid (100 mL), and 50% hypophosphorous acid (55 mL) was refluxed for 5 days. The mixture was then cooled to room temperature and poured into ice water (800 mL). Thereafter, the precipitate was filtered and washed with water and ethanol. The precipitate was then re-crystallized from toluene (620 mL) to give 14.49 g of pale yellow flake-like crystals of 2,6-dibromoanthracene (Compound 24).

Example 2

Synthesis of Bis-(4'-methyl-thiophen-2'yl)-2,6-anthracene

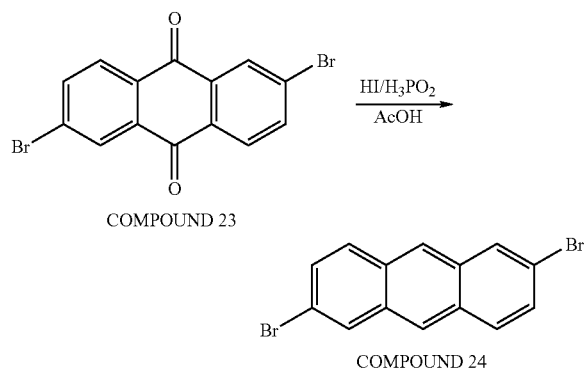

2-(4-Methyl-thiophen-2-yl)-[1,3,2]dioxaborinane: To a solution of 3-methylthiophene (10.0 g, 0.1 mol) in 120 ml of anhydrous diethyl ether was added 2.5 M n-BuLi in hexane (40 ml, 0.1 mol) at room temperature. After stirring at room temperature for 30 min, the resulting solution was refluxed for 1 h. The mixture was cooled down to −76° C. and trimethylborate (16.72 ml, 150 mol) was added slowly. The mixture was allowed to warm to room temperature and stirred for 2 h. After quenching with 10% HCl (150 ml), the organic layer was separated and the aqueous layer was extracted with ether (2×). The combined organic layer was dried over MgSO4, filtered and concentrated. The residue was added to 1,3-propanediol (7.3 ml, 0.1 mol) and refluxed for 3 h. The mixture was then placed directly on a silica column and eluted with hexane, then chloroform to give the product, 12.86 g, 71%. 1H NMR (CDCl3-d3, 500 MHz): δ 7.32 ppm (s, 1 H), 7.11 ppm (s, 1 H), 4.14-4.12 ppm (t, 4 H, J=8.6 Hz), 2.40 (s, 3 H), 2.04 ppm (m, 2 H); 13C-NMR (CDCl3, 500 MHz): δ 138.8, 137.8, 127.03 127.02, 62.09, 27.48, 15.23 ppm. EI, MS m/z (%): 182 (100, M+).

A solution of 2,6-dibromoanthracene (1.68 g, 5.0 mmol) and 2-benzo[b]thiophen-2-yl-[1,3,2]dioxaborinane (3.27 g, 15 mmol) dissolved in toluene (80 ml) was prepared. Sodium carbonate (2.12 g, 20 mmol) dissolved in water (10 ml) was added to this solution. Subsequently, a phase-transfer agent, Aliquat® 336 (0.8 g, 2.0 mmol) was added to the solution. The mixture was bubbled with nitrogen for 15 minutes. Thereafter, tetrakis(triphenylphosphine)palladium(0) (110 mg, 2% mol) was added. The mixture was heated to 90° C. for three days under a nitrogen atmosphere. The reaction mixture was then cooled to room temperature and poured into methanol (600 ml). The yellow precipitate was filtered off, washed with water, dilute acid (5% HCl), methanol, and then with acetone three times to remove the starting material and the mono-substituted by-product.

The crude product was purified by sublimation (270° C./60 mtorr) in a 3-zone furnace. Finally, the purified product was recrystallized from mixed xylene isomers containing ortho-, para- and meta-xylene isomers (Aldrich, Cat. 32057-9) to give 1.49 g (67%) of bright yellow crystals of 2,6-anthracene-bis-2'-benzothiophene (Compound 7).

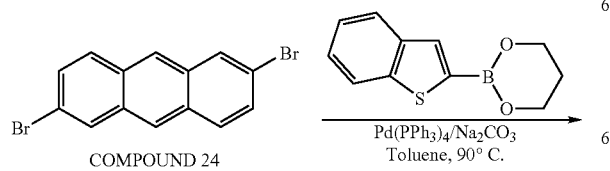

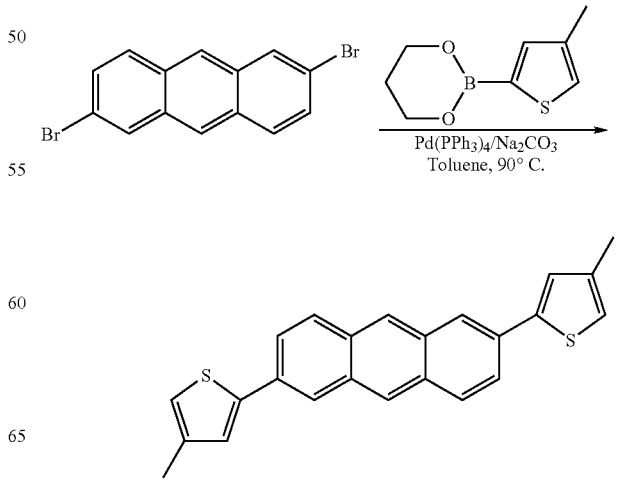

Bis-(4'-methyl-thiophen-2'yl)-2,6-anthracene: To a mixture of 2,6-dibromoanthracene (prepared as in Example 1, 3.36 g, 10.0 mmol) and 2-(4-methyl-thiophen-2-yl)-[1,3,2] dioxaborinane (5.46 g, 30 mmol) in toluene (150 ml) was added Na2CO3 (5.30 g, 50 mmol) dissolved in water (25 ml), followed by the addition of phase-transfer agent Aliquat® 336 (2 g, 5 mmol). The mixture was bubbled with nitrogen for 15 min. Then, tetrakis(triphenylphosphine)palladium(0) (232 mg, 2% mol) was added. The mixture was heated to 90° C. for three days under a nitrogen atmosphere. The reaction mixture was cooled to room temperature and poured into methanol (300 ml). The yellow precipitate was filtered off, washed with water, dilute acid (5% HCl), water, methanol, then with acetone (3×) to remove the starting material and the mono-substituted by-product. The crude product was purified in a 3-zone furnace sublimation and then by recrystallization from xylenes to give 0.97 g (26%) of bright yellow product. EI, MS m/z (%): 370 (100, M+).

Example 3

Synthesis of Bis-(4'-butyl-thiophen-2'yl)-2,6-anthracene

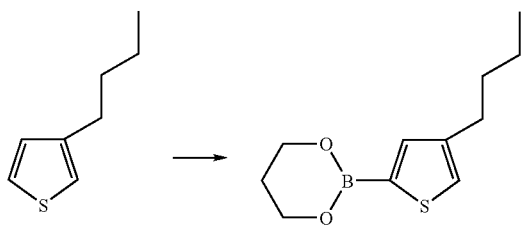

2-(4-Butyl-thiophen-2-yl)-[1,3,2]dioxaborinane: To a solution of diisopropylamine (21.6 ml, 154.0 mmol) in 200 ml of anhydrous diethyl ether was added 2.5 M n-BuLi in hexane (49.3 ml, 123.3 mmol) at room temperature. After stirring at room temperature for 30 min, the resulting lithium di-isopropylamide (LDA) solution was cooled to −76° C. A solution of 3-butylthiophene (18.0 g, 123.3 mmol) in 100 ml of ether was cooled to −76° C. and added to the above LDA solution. The temperature was allowed to rise slowly to −40° C., whereupon it was stirred for 1 h. The solution was then recooled to −76° C. and trimethylborate (20.6 ml, 185.0 mmol) was added slowly. The mixture was allowed to warm to room temperature and stirred for 2 h. After quenching with 10% HCl (180 ml) the organic layer was separated and the aqueous layer was extracted with ether (2×). The combined organic layer was dried over MgSO4, filtered and concentrated. The residue was added to 1,3-propanediol (8.9 ml, 123.3 mmol) and refluxed for 2 h. The mixture was then placed directly on a silica column and eluted first with hexane, then chloroform to give the product, 8.46 g, 31%. 1H NMR (CDCl3-d3, 500 MHz): δ 7.36 ppm (s, 1 H), 7.12 ppm (s, 1 H), 4.14-4.12 ppm (t, 4 H, J=8.6 Hz), 2.60-2.63 ppm (t, 2 H, J=8.6 Hz), 2.04 ppm (m, 2 H), 1.35 ppm (m, 2 H), 1.32 ppm (m, 2 H), 0.89 ppm (t, 3 H, J=7.5 Hz); 13C-NMR (CDCl3, 500 MHz): δ 144.4, 136.8, 126.5 126.4, 62.1, 32.85, 29.73, 27.46, 22.45, 13.90 ppm. EI, MS m/z (%): 224 (100, M+).

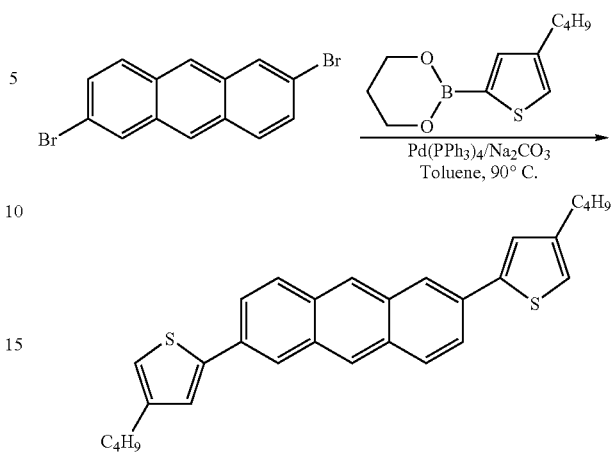

Bis-(4'-butyl-thiophen-2'yl)-2,6-anthracene: To a mixture of 2,6-dibromoanthracene (prepared as described in Example 1, 2.016 g, 6.0 mmol) and 2-(4-butyl-thiophen-2-yl)-[1,3,2] dioxaborinane (4.034 g, 18.0 mmol) in toluene (90 ml) was added Na2CO3 (3.18 g, 30 mmol) dissolved in water (15 ml), followed by the addition of phase-transfer agent Aliquat® 336 (1.2 g, 3.0 mmol). The mixture was bubbled with nitrogen for 15 min. Then, tetrakis(triphenylphosphine)palladium (0) (139 mg, 2% mol) was added. The mixture was heated to 90° C. for three days under a nitrogen atmosphere. The reaction mixture was cooled to room temperature and poured into methanol (300 ml). The yellow precipitate was filtered off, washed with water, dilute acid (5% HCl), water, methanol, then with acetone (3×) to remove the starting material and mono-substituted by-product. The crude product was purified by 3-zone furnace sublimation and finally by recrystallization from xylenes to give 0.68 g (25%) of bright yellow product. 1H NMR (CDCl3-d3, 500 MHz): δ 8.34 ppm (s, 2 H), 8.14 ppm (s, 2 H), 7.97-7.95 ppm (d, 2 H, J=8.5 Hz), 7.72-7.70 ppm (d, 2 H, J=8.5 Hz), 7.31 ppm (s, 2 H), 6.92 ppm (s, 2 H), 2.65-2.68 ppm (t, 4 H, J=8.6 Hz), 1.68 ppm (m, 4H), 1.45 ppm (m, 4 H), 0.89 ppm (t, 6 H, J=7.5 Hz); 13C-NMR (CDCl3, 500 MHz): δ 144.8, 144.5, 132.3, 132.0, 131.9, 131.8, 129.0, 126.6, 125.4, 125.0, 124.0, 120.3, 33.01, 30.74, 22.76, 14.19 ppm. EI, MS m/z (%): 454 (100, M+); HRMS found: 454.1776. Cacld, C30 H30S2: 454.1789. Anal., Found: C, 79.55; H, 6.74; S, 14.56.

Example 4

Synthesis of Bis-(4'-hexyl-thiophen-2'yl)-2,6-anthracene

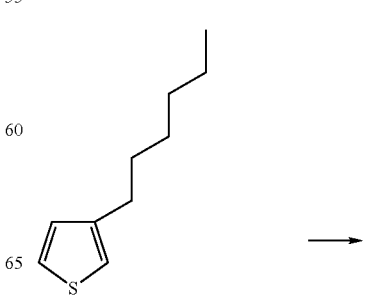

-continued

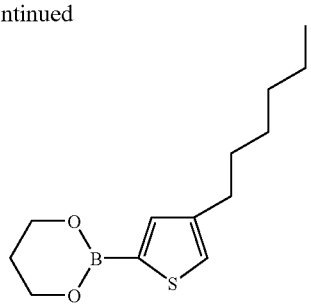

2-(4-Hexyl-thiophen-2-yl)-[1,3,2]dioxaborinane: To a solution of diisopropylamine (9.0 ml, 64.21 mmol) in 100 ml of anhydrous diethyl ether was added 2.5 M n-BuLi in hexane (20.5 ml, 51.2 mmol) at room temperature. After stirring at room temperature for 30 min, the resulting LDA solution was cooled to −76° C. A solution of 3-hexylthiophene (8.617 g, 51.2 mmol) in 100 ml of diethyl ether was cooled to −76° C. and added to the above LDA solution. The temperature was allowed to rise slowly to −40° C., whereupon it was stirred for 1 h. The solution was then recooled to −76° C. and trimethylborate (8.6 ml, 76.8 mmol) was added slowly. The mixture was allowed to warm to room temperature and stirred for 2 h. After quenching with 10% HCl (100 ml) the organic layer was separated and the aqueous layer was extracted with ether (2×). The combined organic layer was dried over MgSO4, filtered and concentrated. The residue was added 1,3-propanediol (3.7 ml, 51.2 mmol) and refluxed for 2 h. The mixture was then placed directly on a silica column and eluted first with hexane, then chloroform to give the product, 2.82 g, 22%. 1H NMR (CDCl3-d3, 500 MHz): δ 7.36 ppm (s, 1 H), 7.13 ppm (s, 1 H), 4.14-4.12 ppm (t, 4 H, J=8.6 Hz), 2.60-2.63 ppm (t, 2 H, J=8.6 Hz), 2.04 ppm (m, 2 H), 1.60 ppm (m, 2H), 1.28 ppm (m, 4 H), 0.87 ppm (t, 3 H, J=7.5 Hz); 13C-NMR (CDCl3, 500 MHz): δ 144.9, 137.2, 126.8, 126.7, 62.50, 32.09, 31.04, 30.48, 29.38, 27.87, 22.99, 14.46 ppm. EI, MS m/z (%): 252 (100, M+).

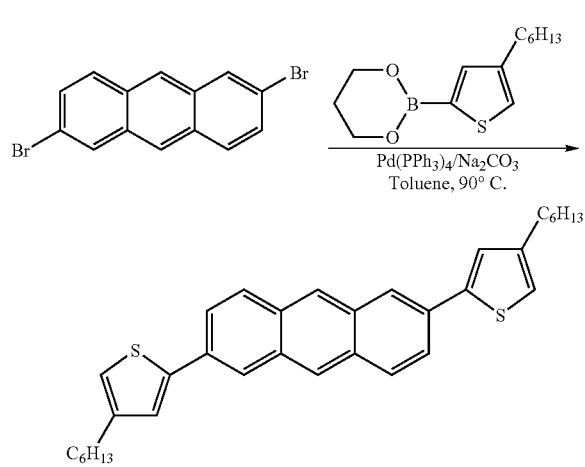

Bis-(4'-hexyl-thiophen-2'yl)-2,6-anthracene: To a mixture of 2,6-dibromoanthracene (prepared as described in Example 1, 1.5829 g, 4.71 mmol) and 2-(4-hexyl-thiophen-2-yl)-[1,3,2]dioxaborinane (2.82 g, 11.18 mmol) in toluene (75 ml) was added Na2CO3 (2.12 g, 20 mmol) dissolved in water (10 ml) followed by the addition of phase-transfer agent Aliquat® 336 (1.0 g, 2.5 mmol). The mixture was bubbled with nitrogen for 15 min. Then, tetrakis(triphenylphosphine)palladium (0) (110 mg, 2% mol) was added. The mixture was heated to 90° C. for three days under a nitrogen atmosphere. The reaction mixture was cooled to room temperature and poured into methanol (300 ml). The yellow precipitate was filtered off, washed with water, dilute acid (5% HCl), water, methanol, then with acetone (3×) to remove the starting material and mono-substituted by-product. The crude product was purified by 3-zone furnace sublimation and finally by recrystallization from xylenes to give 0.50 g (21%) of bright yellow product.

1H NMR (CDCl3-d3, 500 MHz): δ 8.35 ppm (s, 2 H), 8.15 ppm (s, 2H), 7.82-7.95 ppm (d, 2 H, J=8.5 Hz), 7.71-7.79 ppm (d, 2 H, J=8.5 Hz), 7.32 ppm (s, 2 H), 6.92 ppm (s, 2 H), 2.60-2.67 ppm (t, 4 H, J=8.6 Hz), 1.71 ppm (m, 4 H), 1.33-1.43 ppm (m, 12 H), 0.89 ppm (t, 6 H, J=7.5 Hz); 13C-NMR (CDCl3, 500 MHz): δ 145.6, 143.7, 132.7, 132.3, 131.2, 130.0, 129.8, 126.7, 125.8, 125.0, 124.1, 32.46, 32.38, 31.31, 29.54, 23.36, 14.53 ppm. EI, MS m/z (%): 510 (100, M+); HRMS found: 510.2416. Analysis, Found: C, 80.30; H, 7.74; S, 12.84.

Example 5

Synthesis of Bis-(3'-hexyl-thiophen-2'-yl)-2,6-anthracene

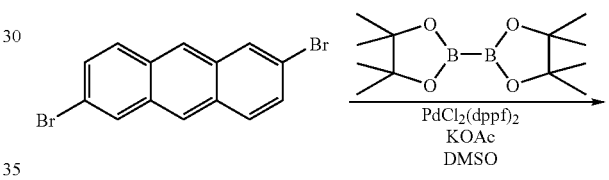

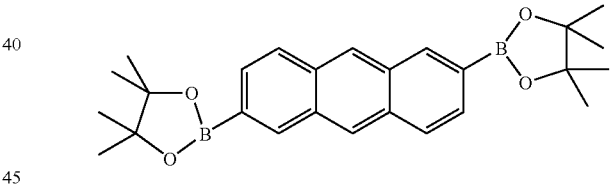

2,6-Anthracene-bis-4,4,5,5-tetramethyl-1,3,2-dioxaborolane. A nitrogen-flushed round bottom flask was charged with 2,6-dibromoanthracene (prepared as in Example 1, 21.73 g, 64.67 mmol), bis(pinacolato)diboron (41.06 g, 161.67 mmol), potassium acetate (25.90 g, 263.85 mmol) and [1,1'-bis(diphenylphosphino)ferrocene]-dichloropalladium complex with dichloromethane (1:1) (1.64 g, 2.0 mmol). Dimethyl sulfoxide (DMSO, 300 ml) was then added and the mixture was bubbled with nitrogen for 15 min. After heating at 80° C. for 16 h, the reaction mixture was cooled to room temperature and poured into ice-water (600 ml). It was then extracted with methylene chloride (2×) and the combined organic layer was dried over anhydrous magnesium sulfate. The solvent was removed by rotary evaporation and the residue was purified several times by flash silica gel column with chloroform/hexane (1:2 to 1:1 to 2:1 to chloroform) as eluent to give 13.4698 g of (48%) bright yellow fine crystals. mp: >260° C. 1H NMR (CDCl3, 500 MHz): δ 8.56 ppm (s, 2 H), 8.44 ppm (s, 2 H), 7.99-7.97 ppm (d, 2 H, J=8.5 Hz), 7.79-7.77 ppm (d, 2 H, J=8.5 Hz), δ 1.41 ppm (s, 24 H); 13C-NMR (CDCl3, 500 MHz): δ 137.7, 133.1, 132.2, 129.5, 127.8, 127.5, 84.37, 25.33 ppm. EI, MS m/z (%): 430 (100, M+). Anal. Found: C, 71.76; H, 7.32; B, 4.89.

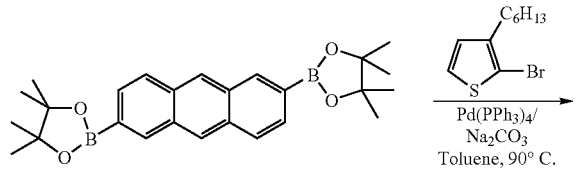

8.42 ppm (s, 2H), 8.04-8.01 ppm (m, 4 H), 7.58 ppm (d, 2 H, J=1.5 Hz), 7.57 ppm (d, 2H, J=1.5 Hz), 7.28 ppm (d, 2 H), 2.76-2.79 ppm (t, 4 H, J=8.6 Hz), 1.66 ppm (m, 4 H), 1.26-1.33 ppm (m, 12 H), 0.89 ppm (t, 6 H, J=7.5 Hz); 13C-NMR (CDCl3, 500 MHz): δ 145.6, 143.7, 132.7, 132.3, 131.2, 130.0, 129.8, 126.7, 125.8, 125.0, 124.1, 32.46, 32.38, 31.31, 29.54, 23.36, 14.53 ppm. EI, MS m/z (%): 510 (100, M+); HRMS found: 510.2416. Anal. Found: C, 80.30; H, 7.74; S, 12.84.

Example 6

Synthesis of 2,6-Anthracene-bis-2'-5'-hexylthiophene

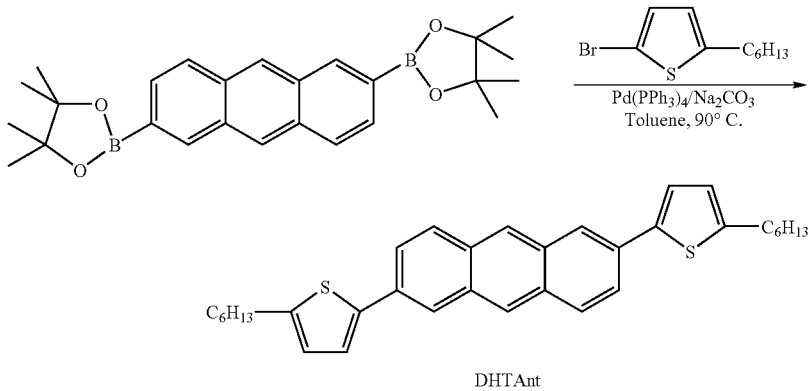

DHTAnt

-continued

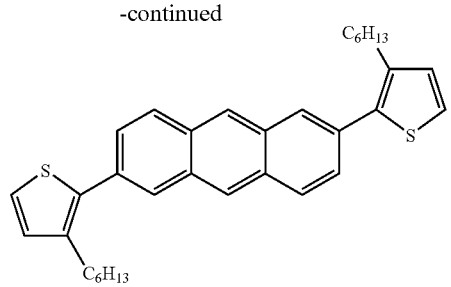

Bis-(3'-hexyl-thiophen-2'-yl)-2,6-anthracene: To a solution of 2,6-anthracene-bis-4',4',5',5'-tetramethyl-1',3',2'-dioxaborolane (1.72 g, 4 mmol) and 2-bromo-3-hexylthiophene (2.966 g, 12 mmol) dissolved in toluene (60 ml) was added Na2CO3 (2.12 g, 20 mmol) dissolved in water (10 ml) followed by the addition of phase-transfer agent Aliquat® 336 (0.82 g, 2.0 mmol). The mixture was bubbled with nitrogen for 15 min. Then, tetrakis(triphenylphosphine)palladium (0) (92.5 mg, 2% mol) was added. The mixture was heated to 90° C. for three days under a nitrogen atmosphere. The reaction mixture was cooled to room temperature and poured into methanol (300 ml). The yellow precipitate was filtered off, washed with water, dilute acid (5% HCl), water, methanol, then with acetone (3×) to remove the starting material and mono-substituted by-product. The crude product was purified on a silica column (eluent: hexane) to give 0.847 g (41%) of bright yellow product. 1H NMR (CDCl3-d3, 500 MHz): δ

2,6-Anthracene-bis-2'-5'-hexylthiophene (DHTAnt). To a solution of 2,6-anthracene-bis-4',4',5',5'-tetramethyl-1',3',2'-dioxaborolane (prepared as in Example 5, 6.8220 g, 15.86 mmol) and 2-bromo-5-hexylthiophene (8.6251 g, 34.89 mmol) dissolved in toluene (240 ml) was added sodium carbonate (8.48 g, 80 mmol) dissolved in water (40 ml) followed by the addition of phase-transfer agent Aliquat® 336 (3.2 g, 8.0 mmol). The mixture was bubbled with nitrogen for 15 min. Then, tetrakis(triphenylphosphine)palladium(0) (368 mg, 2% mol) was added. The mixture was heated to 90° C. for three days under a nitrogen atmosphere. The reaction mixture was cooled to room temperature and poured into methanol (600 ml). The yellow precipitate was filtered off, washed with water, dilute acid (5% HCl), water, methanol, then with acetone (3×) to remove the starting material and mono-substituted by-product. The crude product was purified by sublimation (270° C./60 mmTorr) in a 3-zone furnace, followed by recrystallization from xylenes to give 4.2802 g (53%) of bright yellow product. 1H NMR (p-dichlorobenzene-d4, 500 MHz): δ 8.15 ppm (s, 2 H), 8.01 ppm (s, 2 H), 7.82-7.80 ppm (d, 2 H, J=8.5 Hz), 7.61-7.59 ppm (d, 2 H, J=8.5 Hz), 7.19 ppm (d, 2 H, J=3.45 Hz), 7.02 ppm (d, 2 H, J=3.45 Hz), 6.71 ppm (s, 2H), 2.80-2.77 ppm (t, 2 H, J=8.6 Hz), 1.70 ppm (m, 2 H), 1.32 ppm (m, 6H), 0.89 ppm (t, 3 H, J=7.5 Hz); 13C-NMR (CDCl3, 500 MHz): δ 146.6, 142.7, 132.8, 132.4, 132.2, 130.2, 129.3, 126.8, 125.9, 125.1, 124.0, 32.36, 32.28, 31.11, 29.64, 23.33, 14.63 ppm. EI, MS m/z (%): 510 (100, M+); HRMS found: 510.241463.

Compounds 9-15 were synthesized in a similar manner as that described for the synthesis of DHTAnt.

Example 7

Stability Test for an OTFT Fabricated Using DHTAnt

An OTFT was fabricated using organic semiconductor DHTAnt (2,6-anthracene-bis-2'-5'-hexylthiophene, prepared as described in Example 6) as an active layer in a top contact device as shown in FIG. 1A.

The organic thin film field effect transistor (OTFT) device was fabricated on a heavily doped n-type Si wafer with 200 nm thermal oxide on the top surface, which acts as a dielectric layer with a capacitance per unit area of $1.73 \times 10^{-8}$ F/cm2 and an etched heavily doped n-type Si as a back contact (gate electrode). The wafers were cleaned through subsequent washing with acetone, isopropanol, and deionized water, blown dry with N2 gas, and cleaned in oxygen plasma for 6 min. Then the wafer SiO2 surface was treated with a self-assembling monolayer (SAM) of octyltrichlorosilane (OcTS) by immersing the cleaned wafer substrate in 0.1 M solution of OcTS in toluene at 60° C. for 15 min. After rinsing with toluene and blowing dry with N2 gas, the substrate was annealed at 150° C. for 5 min to crosslink the SAM layers (the contact angle of OcTS treated surface is about 88°~91°). The semiconductor layer was deposited over the treated dielectric surface through shadow masks (40 shadows each with an area of ca. 1000×1000 μm to define the active layers). The organic semiconductors were deposited at a rate of 1-2 Å/s under a pressure of $\sim 2.0 \times 10^{-6}$ Torr to a final thickness of 400 Å determined by a quartz crystal monitor. The film thicknesses were corrected with a stylus profilometer. The substrate temperature during deposition was controlled by heating or cooling the copper block where the substrate was mounted. Gold electrodes were deposited after semiconductor deposition by using shadow masks with W/L of ca. 10/1. The mask defined eight sets of source-drain pairs, each with channel widths of W 400, 600, 800, 1000 μm, respectively and their corresponding eight different channel lengths L 40, 60, 80, and 100 μm, respectively. The electrical characteristics were obtained at room temperature in air using an Agilent 4155C semiconductor parameter analyzer. The mobility and threshold voltages were extracted from the standard TFT analysis. The on/off ratio was determined from the current IDS at VGS=−40 V to the current IDS at VGS=+10 V. All the data in Table 1 were obtained by randomly measuring 8 individual TFTs and determining an average value. Standard deviations were in the range of 5-10%.

The device was tested according to procedure as described above, and the data analyzed as described by Ficker et al., J. Appl. Phys. 94, 2638 (2003). The device was subjected to continuous operation under a constant drain-source voltage of −40 V and an alternating gate-source voltage between +40 V and −40 V. It was found that the semiconductor material was stable in the device and the device performance was the same as the initial testing result. The device was in continuous operation for at least 22 hr during the test.

In another test, devices were constructed as described above using DHTAnt in the semiconductor layer and the mobility and on/off ratios were measured periodically over a span of 15 months. The performance was essentially stable over that timeframe. The mobility varied from 0.35 to 0.42 cm2/Volt-sec. The on/off ratio varied from $1.1 \times 10^6$ to $4.7 \times 10^7$. Mobilities were calculated by the method described in U.S. Pat. No. 6,452,207 (col. 9, lines 55-63).

Example 8

Performance of OTFT Devices Prepared from Various Semiconductors

Table 1 lists the OTFT performance data for devices prepared from several different organic semiconductors of Formula 2 deposited at different substrate temperatures. All OTFTs showed very well-defined linear- and saturation-regime output characteristics. Interestingly, these organic semiconductors showed substitutent-dependent charge mobility, with DHTAnt, DOTAnt, DHTTAnt and DOPhTAnt showing higher mobilities above 0.1 cm2/Vs. Other semiconductors showed moderate charge mobilities.

TABLE 1

| SC Material | Substrate Temperature | Top Contact μ (cm2/Vs) | On/Off | Vt (V) |
|---|---|---|---|---|
| DTAnt | 23° C. | 0.037 | $9.15 \times 10^5$ | −13.5 |
| | 60° C. | 0.048 | $7.36 \times 10^6$ | −5.5 |
| | 80° C. | 0.063 | $8.76 \times 10^5$ | −6.6 |
| | 90° C. | 0.035 | $3.82 \times 10^5$ | −3.8 |
| | 100° C. | 0.025 | $2.92 \times 10^5$ | −3.4 |
| DEtTAnt | 23° C. | 0.064 | $1.09 \times 10^5$ | −1.7 |
| | 40° C. | 0.030 | $5.87 \times 10^4$ | −12.6 |
| | 60° C. | 0.0062 | $1.16 \times 10^3$ | 30.3 |
| | 80° C. | 0.0011 | $2.08 \times 10^3$ | −9.9 |
| | 100° C. | 0.000001 | $1.1 \times 10^3$ | −18 |
| DBuTAnt | 23° C. | 0.040 | $4.88 \times 10^6$ | −13.7 |
| | 60° C. | 0.0255 | $2.91 \times 10^6$ | −14.8 |
| | 80° C. | 0.0422 | $5.96 \times 10^7$ | −13.7 |
| | 90° C. | 0.029 | $1.14 \times 10^5$ | −9.0 |
| | 100° C. | 0.078 | $4.77 \times 10^5$ | −2.8 |
| DHTAnt | 23° C. | 0.038 | $4.0 \times 10^6$ | 4.4 |
| | 60° C. | 0.17 | $2.87 \times 10^6$ | 5.1 |
| | 70° C. | 0.161 | $4.40 \times 10^6$ | 4.1 |
| | 80° C. | 0.25 | $1.14 \times 10^6$ | 3.4 |
| | 100° C. | 0.038 | $6.77 \times 10^5$ | 4.9 |
| | 120° C. | 0.041 | $1.7 \times 10^6$ | 3.5 |
| DOTAnt | 23° C. | 0.069 | $5.85 \times 10^6$ | 3.7 |
| | 60° C. | 0.104 | $4.70 \times 10^5$ | 3.0 |
| | 100° C. | 0.175 | $3.40 \times 10^7$ | −3.4 |
| | 80° C. | 0.181 | $6.28 \times 10^6$ | −1.3 |
| DHTTAnt | 23° C. | 0.070 | $1.54 \times 10^5$ | −4.1 |
| | 60° C. | 0.174 | $1.58 \times 10^3$ | −5.6 |
| | 80° C. | 0.123 | $7.69 \times 10^5$ | 0 |
| | 100° C. | 0.079 | $2.93 \times 10^5$ | 3.6 |
| DBTAnt | 23° C. | 0.00003 | $2.13 \times 10^5$ | 3.77 |
| | 80° C. | 0.007 | $4.13 \times 10^5$ | 4.42 |
| DOPhTAnt | 23° C. | 0.049 | $1.03 \times 10^5$ | −0.6 |
| | 60° C. | 0.051 | $5.12 \times 10^4$ | −0.8 |
| | 80° C. | 0.0565 | $1.24 \times 10^5$ | 0.8 |
| | 100° C. | 0.195 | $1.06 \times 10^6$ | 1.0 |
| | 120° C. | 0.054 | $1.71 \times 10^3$ | 3.5 |
| | 140° C. | 0.194 | $5.79 \times 10^5$ | −3.4 |

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims.

What is claimed is:

1. An OTFT comprising:

a. a substrate b. an insulating layer;

c. a gate electrode;
d. a source electrode;
e. a drain electrode; and
f. an organic semiconductor layer comprising a compound of Formula 2,

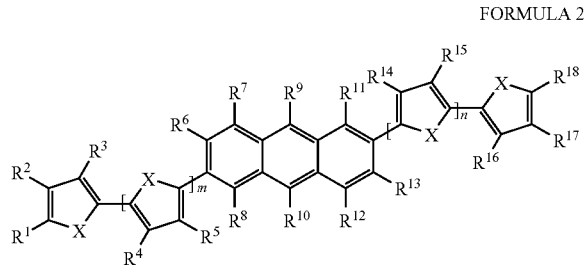

FORMULA 2 wherein
m and n are integers selected independently from 0-10;
X is selected independently from O, Te, Se and NR;
$R^1$-$R^{18}$ are selected independently from hydrogen; substituted and unsubstituted alkyl; substituted and unsubstituted aryl; substituted and unsubstituted heteroaryl; halogen; hydroxy; substituted and unsubstituted aryloxy; substituted and unsubstituted alkoxy; substituted and unsubstituted alkenyl; substituted and unsubstituted alkynyl; substituted and unsubstituted amino; substituted and unsubstituted alkylthio; substituted and unsubstituted phosphino; substituted and unsubstituted silyl; —COR; —COOR; —$PO_3R_2$; —$OPO_3R_2$; —CN; —$C_nF_{2n+1}$; and —$C_nF_{2n+1}C_mH_{2m+1}$, wherein any two adjacent groups, $R^1$-$R^{18}$ can be taken together to form a ring; and
R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted or unsubstituted amino and wherein the insulating layer, the gate electrode, the organic semiconductor layer, the source electrode and the drain electrode are arranged in any sequence, provided that the gate electrode and the organic semiconductor layer both contact the insulating layer, the source electrode and the drain electrode both contact the organic semiconductor layer and the electrodes are separated from each other.

2. The OTFT of claim 1, wherein the substituted R and substituted $R^1$-$R^{18}$ groups have substituent groups selected from cyanide groups; nitro groups; ester groups; ether groups; halogen substitutents; hydroxy groups; alkyl groups; aryl groups; silyl groups; and alkoxy groups.

3. The OTFT of claim 1, wherein $R^9$ and $R^{10}$ are each H.

4. The OTFT of claim 1, wherein the substrate comprises a material selected from inorganic glasses, ceramic foils, acrylics, epoxies, polyamides, polycarbonates, polyimides, polyketones, poly(oxy-1,4-phenyleneoxy-1,4-phenylenecarbonyl-1,4-phenylene), polynorbornenes, polyphenyleneoxides, poly(ethylene naphthalenedicarboxylate), poly(ethylene terephthalate), poly(phenylene sulfide), fiber-reinforced plastics, and coated metallic foils.

5. The OTFT of claim 1, wherein the gate electrode comprises a material selected from doped silicon; aluminum; gold; chromium; indium tin oxide; polystyrene sulfonate-doped poly(3,4-ethylenedioxythiophene) (PSS-PEDOT); carbon black or graphite dispersed in a polymer binder; and a colloidal silver dispersion in a polymer binder.

6. The OTFT of claim 1, wherein the source and drain electrodes comprise a material selected from aluminum, barium, calcium, chromium, gold, silver, nickel, palladium, platinum, titanium, and alloys thereof; carbon nanotubes; polyaniline; poly(3,4-ethylenedioxythiophene)/poly-(styrene sulfonate) (PEDOT:PSS); dispersions of carbon nanotubes in conducting polymers; dispersions of a metal in a conducting polymer; and multilayers thereof.

7. The OTFT of claim 1, wherein the insulating layer comprises a material selected from aluminum oxides, silicon oxides, tantalum oxides, titanium oxides, silicon nitrides, barium titanate, barium strontium titanate, barium zirconate titanate, zinc selenide, zinc sulfide, and alloys, combinations, and multilayers thereof; polyesters, polycarbonates, poly(vinyl phenol), polyimides, polystyrene, poly(methacrylate)s, poly(acrylate)s, epoxy resins, and blends and multilayers thereof.

8. An OTFT comprising:
a. a substrate
b. an insulating layer;
c. a gate electrode;
d. a source electrode;
e. a drain electrode; and
f. an organic semiconductor layer comprising a compound of Formula 2,

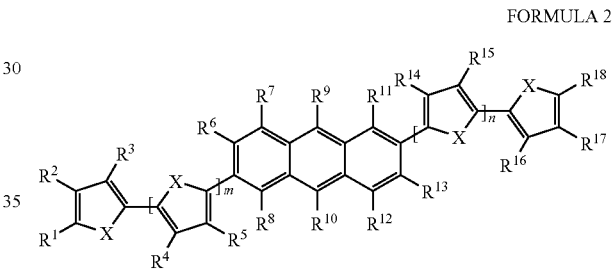

FORMULA 2 wherein
m and n are integers selected independently from 0-10;
X is selected independently from O, S, Te, Se and NR;
$R^1$-$R^{18}$ are selected independently from hydrogen; substituted and unsubstituted alkyl; substituted and unsubstituted aryl; substituted and unsubstituted heteroaryl; halogen; hydroxy; substituted and unsubstituted aryloxy; substituted and unsubstituted alkoxy; substituted and unsubstituted alkenyl; substituted and unsubstituted alkynyl; substituted and unsubstituted amino; substituted and unsubstituted alkylthio; substituted and unsubstituted phosphino; substituted and unsubstituted silyl; —COR; —COOR; —$PO_3R_2$; —$OPO_3R_2$; —CN; —$C_nF_{2n+1}$; and —$C_nF_{2n+1}C_mH_{2m+1}$, wherein any two adjacent groups, $R^1$-$R^{18}$ can be taken together to form a ring; and
R is selected from hydrogen; substituted and unsubstituted alkyl; substituted and unsubstituted aryl; substituted and unsubstituted heteroaryl; substituted and unsubstituted alkenyl; substituted and unsubstituted alkynyl; and substituted or unsubstituted amino
with the proviso that adjacent groups $R^1$ and $R^2$, or $R^{17}$ and $R^{18}$, are taken together to form a ring and
wherein the insulating layer, the gate electrode, the organic semiconductor layer, the source electrode and the drain electrode are arranged in any sequence, provided that the gate electrode and the organic semiconductor layer both contact the insulating layer, the source electrode and the drain electrode both contact the organic semiconductor layer and the electrodes are separated from each other.
9. An OTFT comprising:
a. a substrate
b. an insulating layer;
c. a gate electrode;
d. a source electrode;
e. a drain electrode; and
f. an organic semiconductor layer comprising a compound selected from the group consisting of
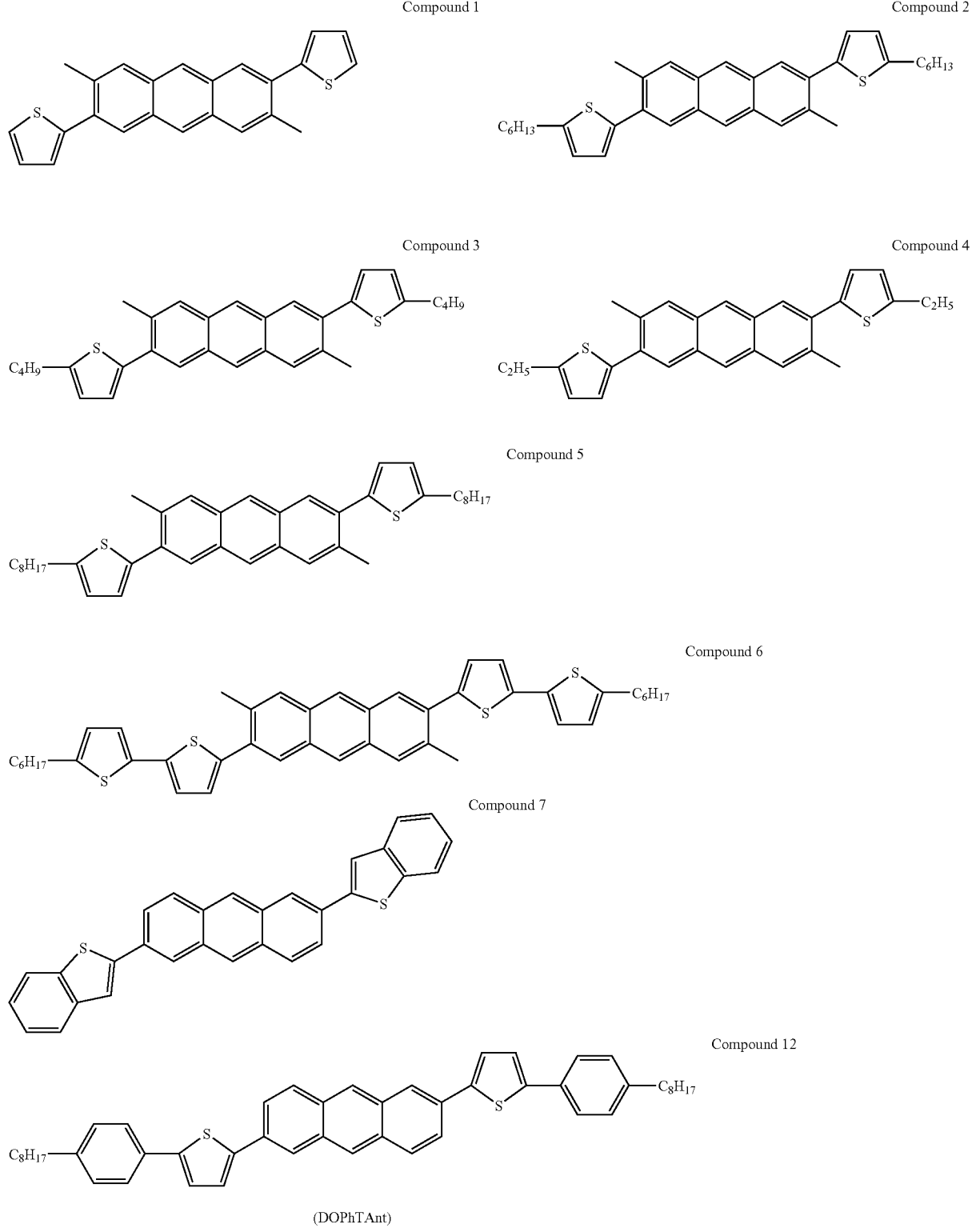

wherein the insulating layer, the gate electrode, the organic semiconductor layer, the source electrode and the drain electrode are arranged in any sequence, provided that the gate electrode and the organic semiconductor layer both contact the insulating layer, the source electrode and the drain electrode both contact the organic semiconductor layer and the electrodes are separated from each other.

* * * * *